United States Patent
Arai et al.

(10) Patent No.: US 11,877,764 B2
(45) Date of Patent: Jan. 23, 2024

(54) CORONARY ARTERY BYPASS SURGERY TREATMENT TOOL, TREATMENT TOOL PART, MEDICAL CONNECTOR, AND MEDICAL DEVICE

(71) Applicants: SUMITOMO BAKELITE CO., LTD., Shinagawa-ku (JP); NATIONAL UNIVERSITY CORPORATION TOKYO MEDICAL AND DENTAL UNIVERSITY, Bunkyo-ku (JP)

(72) Inventors: Hirokuni Arai, Tokyo (JP); Toshifumi Sakate, Akita (JP); Akira Kawamata, Akita (JP); Shinetsu Harata, Akita (JP)

(73) Assignees: SUMITOMO BAKELITE CO., LTD., Shinagawa-ku (JP); NATIONAL UNIVERSITY CORPORATION TOKYO MEDICAL AND DENTAL UNIVERSITY, Bunkyo-ku (JP)

( * ) Notice: Subject to any disclaimer, the term of this patent is extended or adjusted under 35 U.S.C. 154(b) by 871 days.

(21) Appl. No.: 16/614,970

(22) PCT Filed: May 16, 2018

(86) PCT No.: PCT/JP2018/018860
§ 371 (c)(1),
(2) Date: Nov. 19, 2019

(87) PCT Pub. No.: WO2018/216560
PCT Pub. Date: Nov. 29, 2018

(65) Prior Publication Data
US 2020/0197037 A1    Jun. 25, 2020

(30) Foreign Application Priority Data

May 23, 2017  (JP) .................................. 2017-102142
May 23, 2017  (JP) .................................. 2017-102143

(51) Int. Cl.
*A61B 17/30*    (2006.01)
*A61M 39/10*    (2006.01)
*A61B 17/00*    (2006.01)

(52) U.S. Cl.
CPC ............. *A61B 17/30* (2013.01); *A61M 39/10* (2013.01); *A61B 2017/00477* (2013.01);
(Continued)

(58) Field of Classification Search
CPC ...... A61B 2017/0243; A61B 2017/306; A61B 2017/308; A61M 39/10
See application file for complete search history.

(56) References Cited

U.S. PATENT DOCUMENTS 2,082,782 A * 6/1937 Allen ..................... A61B 17/28
                                                           604/176
4,639,019 A * 1/1987 Mittleman ............ F16L 47/041
                                                           285/332
(Continued)

FOREIGN PATENT DOCUMENTS

CN         101039628 A     9/2007
EP         0 151 519 A1    8/1985
(Continued)

OTHER PUBLICATIONS

International Search Report dated Jul. 10, 2018 in PCT/JP2018/018860 filed on May 16, 2018.

*Primary Examiner* — Scott J Medway
(74) *Attorney, Agent, or Firm* — Oblon, McClelland, Maier & Neustadt, L.L.P.

(57) ABSTRACT

The present invention provides a coronary artery bypass surgery treatment tool or the like including a flexible tube, a suction cup in which an opening portion is formed to communicate with the flexible tube and which is provided at a distal end of the flexible tube, a joint portion which has a suction path, a male connector which is provided in one of
(Continued)

a proximal end of the flexible tube and a distal end of the suction path of the joint portion, and a female connector which is provided in the other thereof and is detachably connected to the male connector.

17 Claims, 18 Drawing Sheets

(52) U.S. Cl.
CPC ... *A61B 2017/308* (2013.01); *A61B 2217/005* (2013.01); *A61M 2039/1038* (2013.01); *A61M 2210/125* (2013.01)

(56) References Cited

U.S. PATENT DOCUMENTS

| | | | | |
|---|---|---|---|---|
| 5,019,086 | A * | 5/1991 | Neward | A61B 17/442 606/123 |
| 5,484,391 | A * | 1/1996 | Buckman, Jr. | A61M 60/268 601/153 |
| 5,651,776 | A * | 7/1997 | Appling | A61M 39/10 285/332 |
| 5,727,569 | A * | 3/1998 | Benetti | A61B 17/00 606/1 |
| 5,836,311 | A * | 11/1998 | Borst | A61B 17/02 606/191 |
| 5,865,730 | A * | 2/1999 | Fox | A61B 17/0218 600/227 |
| 5,885,271 | A * | 3/1999 | Hamilton | A61B 17/02 606/1 |
| 5,984,864 | A * | 11/1999 | Fox | A61B 90/57 600/201 |
| 6,019,722 | A * | 2/2000 | Spence | A61B 17/0218 600/210 |
| 6,210,323 | B1 * | 4/2001 | Gilhuly | A61B 17/02 600/210 |
| 6,332,633 | B1 * | 12/2001 | Fitoussi | F16L 15/006 285/332 |
| 6,447,443 | B1 * | 9/2002 | Keogh | A61B 17/0206 600/235 |
| 6,478,729 | B1 * | 11/2002 | Rogers | A61B 17/02 128/898 |
| 6,503,185 | B1 * | 1/2003 | Waksman | A61N 5/1007 604/509 |
| 6,517,563 | B1 * | 2/2003 | Paolitto | A61B 17/02 600/206 |
| 6,893,056 | B2 * | 5/2005 | Guala | F16L 47/04 285/332.1 |
| 7,146,225 | B2 * | 12/2006 | Guenst | A61N 1/0587 607/116 |
| 7,416,527 | B2 * | 8/2008 | Arai | A61B 17/02 600/37 |
| 8,114,009 | B2 * | 2/2012 | Arai | A61B 17/02 600/37 |
| 8,162,817 | B2 * | 4/2012 | Spence | A61B 17/0206 600/37 |
| 8,460,172 | B2 * | 6/2013 | Meyer | A61B 17/0206 600/37 |
| 9,468,362 | B2 * | 10/2016 | Goldfarb | A61B 1/0051 |
| 2002/0092533 | A1 | 7/2002 | Boyd et al. | |
| 2003/0009080 | A1 * | 1/2003 | Peng | A61B 17/02 600/37 |
| 2003/0078470 | A1 * | 4/2003 | Borst | A61B 17/02 606/1 |
| 2004/0138522 | A1 | 7/2004 | Haarstad et al. | |
| 2004/0143153 | A1 | 7/2004 | Sharrow | |
| 2005/0010197 | A1 * | 1/2005 | Lau | A61M 1/80 606/1 |
| 2005/0033110 | A1 * | 2/2005 | Bertolero | A61B 17/0206 600/37 |
| 2005/0049463 | A1 | 3/2005 | Arai et al. | |
| 2007/0129705 | A1 | 6/2007 | Trombley, III et al. | |
| 2008/0195041 | A1 * | 8/2008 | Goldfarb | A61M 25/09 604/528 |
| 2008/0306469 | A1 | 12/2008 | Masuda et al. | |
| 2009/0030270 | A1 | 1/2009 | Arai et al. | |
| 2012/0157788 | A1 * | 6/2012 | Serowski | A61B 90/57 600/229 |
| 2013/0245611 | A1 | 9/2013 | Bonnet et al. | |
| 2015/0005715 | A1 * | 1/2015 | Cowan | A61M 39/12 604/535 |

FOREIGN PATENT DOCUMENTS

| | | |
|---|---|---|
| EP | 2 161 013 A1 | 3/2010 |
| EP | 3 000 503 A1 | 3/2016 |
| JP | 2005-237945 A | 9/2005 |
| JP | 2013-545493 A | 12/2013 |
| JP | 2016-028753 A | 3/2016 |
| WO | WO 2011/159733 A1 | 12/2011 |
| WO | WO 2014/188969 A1 | 11/2014 |

* cited by examiner

CORONARY ARTERY BYPASS SURGERY TREATMENT TOOL, TREATMENT TOOL PART, MEDICAL CONNECTOR, AND MEDICAL DEVICE

TECHNICAL FIELD

The present invention relates to a coronary artery bypass surgery treatment tool, a treatment tool part, a medical connector, and a medical device.

BACKGROUND ART

As a coronary artery bypass surgery treatment tool for holding a heart at a desired position during coronary artery bypass surgery, for example, a coronary artery bypass surgery treatment tool described in PTL 1 is known.

Moreover, PTL 2 describes a medical connector including a male connector and a female connector connected to the male connector. The medical connector of PTL 2 has a structure in which the male connector and the female connector are connected to each other by screwing a female screw disposed around a male luer of the male connector and a screw thread formed on an outer peripheral surface of the female connector.

CITATION LIST

Patent Literature

[PTL 1] Japanese Unexamined Patent Application, First Publication No. 2005-237945
[PTL 2] Japanese Unexamined Patent Application, First Publication No. 2016-28753

SUMMARY OF INVENTION

Technical Problem

However, according to studies of the present inventor, the above-described coronary artery bypass surgery treatment tool still has room for improvement in handling properties. In addition, the medical connector described in PTL 2 has room for improvement in dimensions.

The present invention is made in consideration of the problems, and provides a coronary artery bypass surgery treatment tool and a treatment tool part including a structure having excellent handling properties. Moreover, the present invention provides a medical connector and a medical device having a more compact structure.

Solution to Problem

According to an aspect of the present invention, a coronary artery bypass surgery treatment tool is provided, including: a flexible tube; a suction cup in which an opening portion is formed to communicate with the flexible tube and which is provided at a distal end of the flexible tube; a joint portion which has a suction path; a male connector which is provided in one of a proximal end of the flexible tube and a distal end of the suction path of the joint portion; and a female connector which is provided in the other thereof and is detachably connected to the male connector.

According to another aspect of the present invention, a treatment tool part is provided, including: a flexible tube; a suction cup in which an opening portion is formed to communicate with the flexible tube and which is provided at one end of the flexible tube; a linear body whose one end side is fixed to the one end of the flexible tube or the suction cup; and a female connector which has a hollow accommodation portion and is provided at the other end of the flexible tube, in which the accommodation portion is a female luer which has an opening at one end and in which an inner diameter of the accommodation portion decreases in a depth direction from the opening, and a spiral groove is formed on an inner peripheral surface of the female luer.

According to still another aspect of the present invention, a medical connector is provided, including: a male connector; and a female connector which is connected to the male connector, in which the male connector has a main body portion and an insertion protrusion which is formed to protrude from the main body portion, the female connector has a hollow accommodation portion which accommodates the insertion protrusion, an engaging convex portion is formed in one of an outer peripheral surface of the insertion protrusion and an inner peripheral surface of the accommodation portion, an engaging recessed portion is formed in the other thereof, and the engaging convex portion and the engaging recessed portion are screwed to each other so that the male connector and the female connector are connected to each other.

In addition, according to still another aspect of the present invention, a medical connector is provided which is a hollow female connector having an opening at one end of which an inner diameter decreases in a depth direction from the opening, a protrusion portion is formed in the vicinity of the one end on an outer peripheral surface of the female connector, and a helical recessed groove is formed on an inner peripheral surface of the female connector.

Moreover, according to still another aspect of the present invention, a medical device is provided, including: the medical connector of the present invention.

Advantageous Effects of Invention

According to the present invention, it is possible to improve handling properties of the coronary artery bypass surgery treatment tool. Moreover, according to the present invention, the male connector can be made compact, and as a result, the entire medical connector can be made compact.

BRIEF DESCRIPTION OF DRAWINGS

FIG. 1 is a schematic overall view of a coronary artery bypass surgery treatment tool (medical device) according to Embodiment 2-1.

FIG. 2 is a schematic diagram of a joint portion of the coronary artery bypass surgery treatment tool (medical device) according to Embodiment 2-1.

FIG. 3 is a schematic diagram of a treatment tool part (medical device) of the coronary artery bypass surgery treatment tool according to Embodiment 1-1.

FIG. 4 is a view showing a female connector of a medical connector according to Embodiment 2-1, in which (a) is a side view, (b) is a side view when viewed in the direction of an arrow B in (a), and (c) is a cross-sectional view taken along a central axis of the female connector.

FIG. 5 is a cross-sectional view showing the female connector of the medical connector and a joint portion-side connector according to Embodiment 2-1, and shows a state in which the female connector and the joint portion-side connector are separated from each other.

FIG. 6 is a cross-sectional view showing the female connector of the medical connector and the joint portion-side connector according to Embodiment 2-1, and shows a state in which the female connector and the joint portion-side connector are connected to each other.

FIG. 7 is a cross-sectional view showing the female connector and the male connector of the medical connector according to Embodiment 2-1, and shows a state in which the female connector and the male connector are separated from each other.

FIG. 8 is a cross-sectional view showing the female connector and the male connector of the medical connector according to Embodiment 2-1, and shows a state in which the female connector and the male connector are connected to each other.

FIG. 10 is a schematic view showing a state in which grasping of a protrusion portion of a male connector of a treatment tool part according to Embodiment 2-1 is attempted with forceps.

FIG. 11 is a schematic diagram explaining an example of a treatment using the coronary artery bypass surgery treatment tool according to Embodiment 2-1.

FIG. 12 is a schematic diagram explaining an example of the treatment using the coronary artery bypass surgery treatment tool according to Embodiment 2-1.

FIG. 13 is a schematic view of a treatment tool part (medical device) according to Embodiment 2-2.

FIG. 14 is a cross-sectional view showing a female connector and a male connector of a medical connector according to Embodiment 2-2, and shows a state in which the female connector and the male connector are separated from each other.

DESCRIPTION OF EMBODIMENTS

Figure 1:
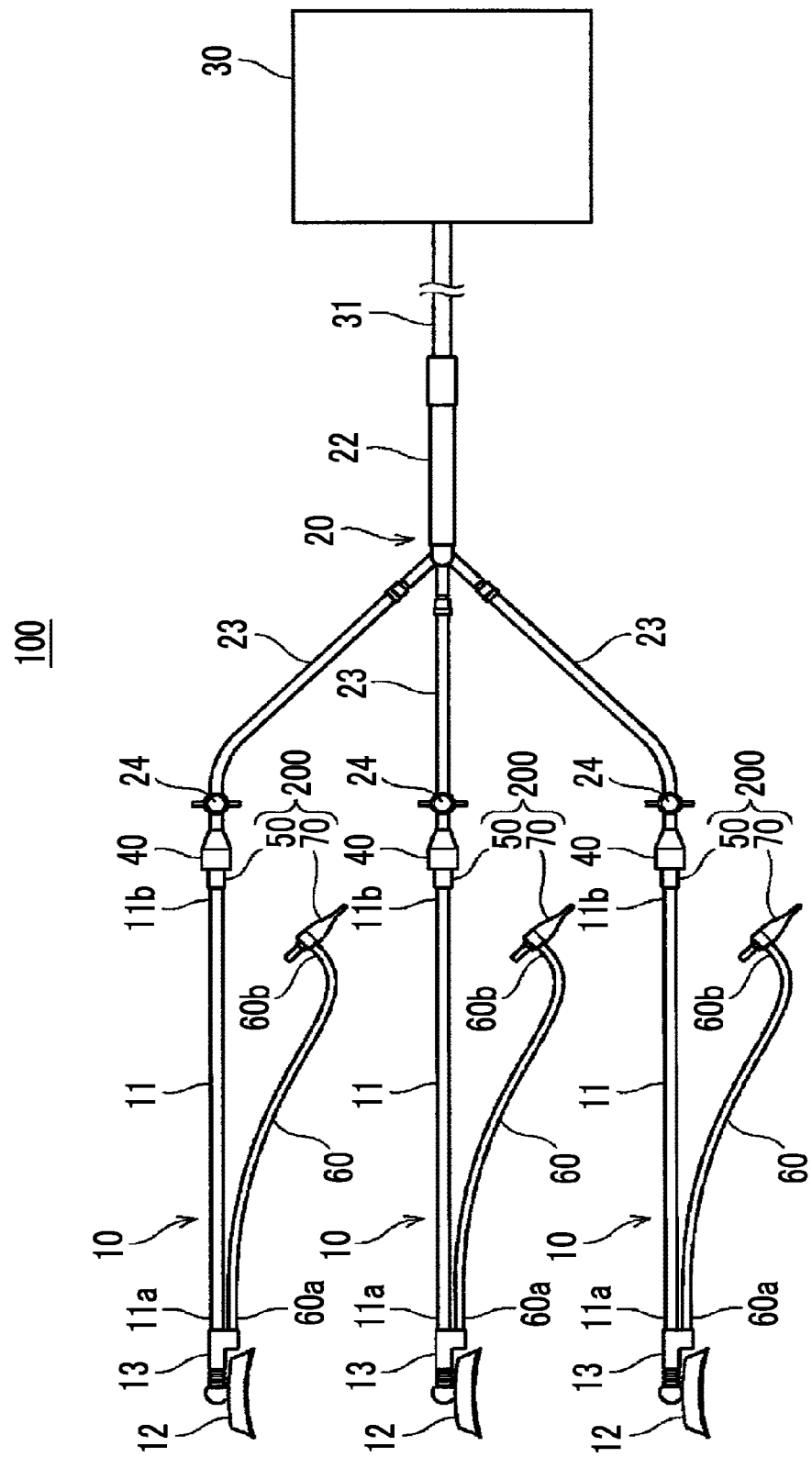
FIG. 1 is a schematic overall view of a coronary artery bypass surgery treatment tool according to Embodiment 1-1. Moreover.

Hereinafter, embodiments of the present invention will be described with reference to the drawings. Moreover, in all the drawings, the same reference signs are assigned to the same components, and descriptions thereof are appropriately omitted.

Embodiment 1-1

First, Embodiment 1-1 will be described with reference to FIGS. 1 to 12(*b*).

A coronary artery bypass surgery treatment tool 100 according the present embodiment includes a flexible tube 11, a suction cup 12 which includes an opening portion 12*a* formed to communicate with the flexible tube 11 and is provided at a distal end 11*a* of the flexible tube 11, a joint portion 20 which has a suction path 21, a male connector 40 which is provided on one of a proximal end 11*b* of the flexible tube 11 and a distal end 21*a* of the suction path 21 of joint portion 20, and a female connector 50 which is provided on the other thereof and is detachably connected to the male connector 40.

According to the coronary artery bypass surgery treatment tool 100 according to the present embodiment, the flexible tube 11 and the joint portion 20 are detachable.

Accordingly, the coronary artery bypass surgery treatment tool 100 has excellent handling properties.

For example, the flexible tube 11 removed from the joint portion 20 is inserted into a thoracic cavity 96 (FIG. 11) from an incision 93 (FIG. 11), the flexible tube 11 is extracted from a small incision hole 95 (FIGS. 12(a) and 12(b)), and the flexible tube 11 can be connected to the joint portion 20. Accordingly, the incision 93 can be made small and it is possible to reduce a burden on a living body.

In addition, respective components of the coronary artery bypass surgery treatment tool 100 according to the present embodiment do not need to exist separately independently. A plurality of components may be formed as one member, a component may be formed of a plurality of members, a component may be a portion of another component, and a portion of a component and a portion of another component may overlap each other.

Hereinafter, the present embodiment will be described in more detail.

As shown in FIG. 1, for example, the coronary artery bypass surgery treatment tool 100 includes a plurality (for example, three) of treatment tool parts 10, the joint portion 20, and a suction source 30.

A suction tube 31 for suction is led out from the suction source 30. A distal end of the suction tube 31 is connected to a proximal end (a proximal end of a main tube 22 described below) of the joint portion 20. In the present specification, the distal end and the proximal end are all based on the suction source 30, a side away from the suction source 30 is the distal end, and a side close to the suction source 30 is the proximal end.

Figure 2:
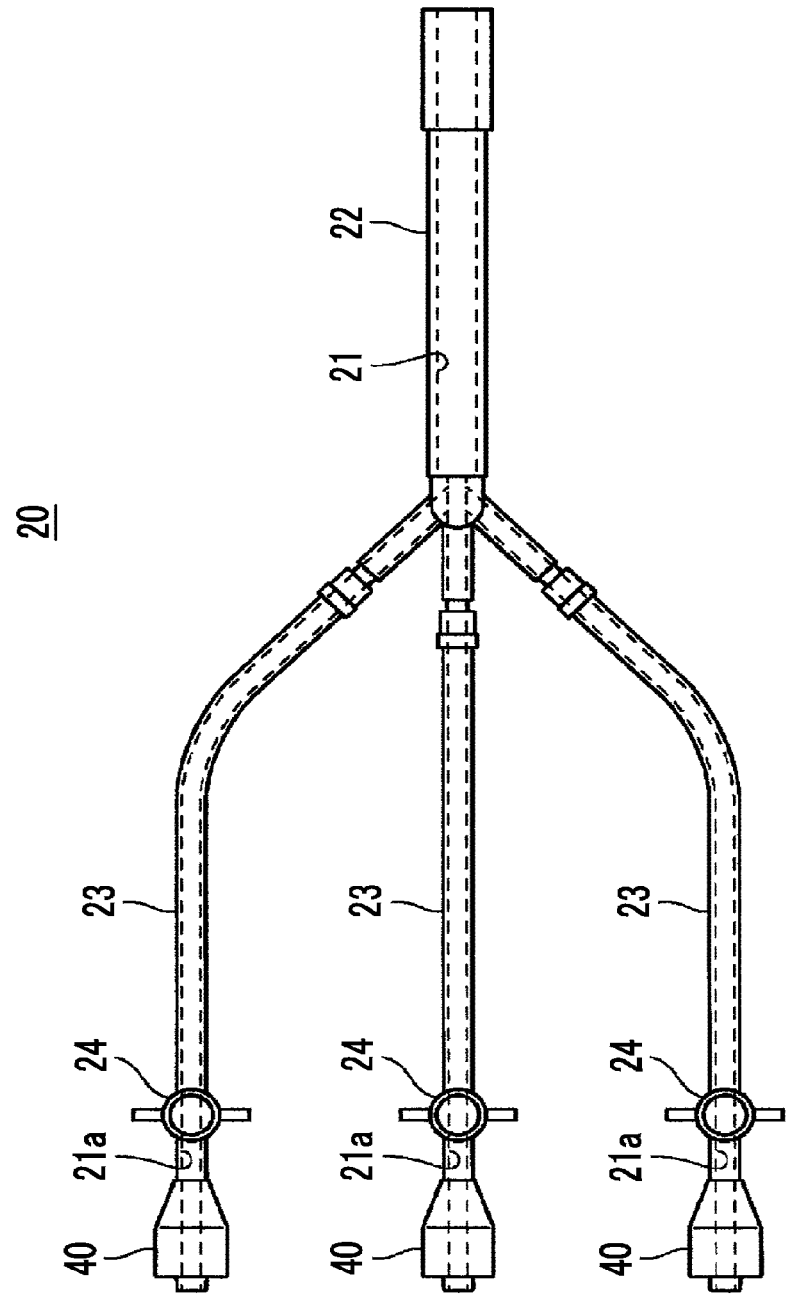
FIG. 2 is a schematic view of a joint portion of the coronary artery bypass surgery treatment tool according to Embodiment 1-1. Moreover.

As shown in FIG. 2, for example, the joint portion 20 includes the main tube 22, and a plurality of (for example, three) secondary tubes 23 divided into a plurality (for example, divided into three tube) of tubes from a distal end of the main tube 22.

The main tube 22 is a tubular member which allows gas to flow through the inside of the main tube 22 from the distal end to the proximal end of the main tube 22.

Moreover, each of the secondary tubes 23 is a tubular member which allows gas to flow through the inside of the secondary tube 23 from a distal end to a proximal end of the secondary tube 23.

The proximal end of each secondary tube 23 communicates with the distal end of the main tube 22. Therefore, a series of suction paths 21 are formed in the joint portion 20 from the proximal end of the main tube 22 to the distal ends of the respective secondary tubes 23.

Each secondary tube 23 has a three-way valve 24 for performing switching between an open state in which the gas can flow through the secondary tube 23 and a closed state in which the flow of the gas in the secondary tube 23 is blocked.

A male connector 40 is provided at the distal end (that is, the distal end of the joint portion 20) of each secondary tube 23, and the male connector 40 communicates with the suction path 21. That is, in the present embodiment, the male connector 40 is provided at the distal end of the suction path 21 of the joint portion 20.

Figure 5:
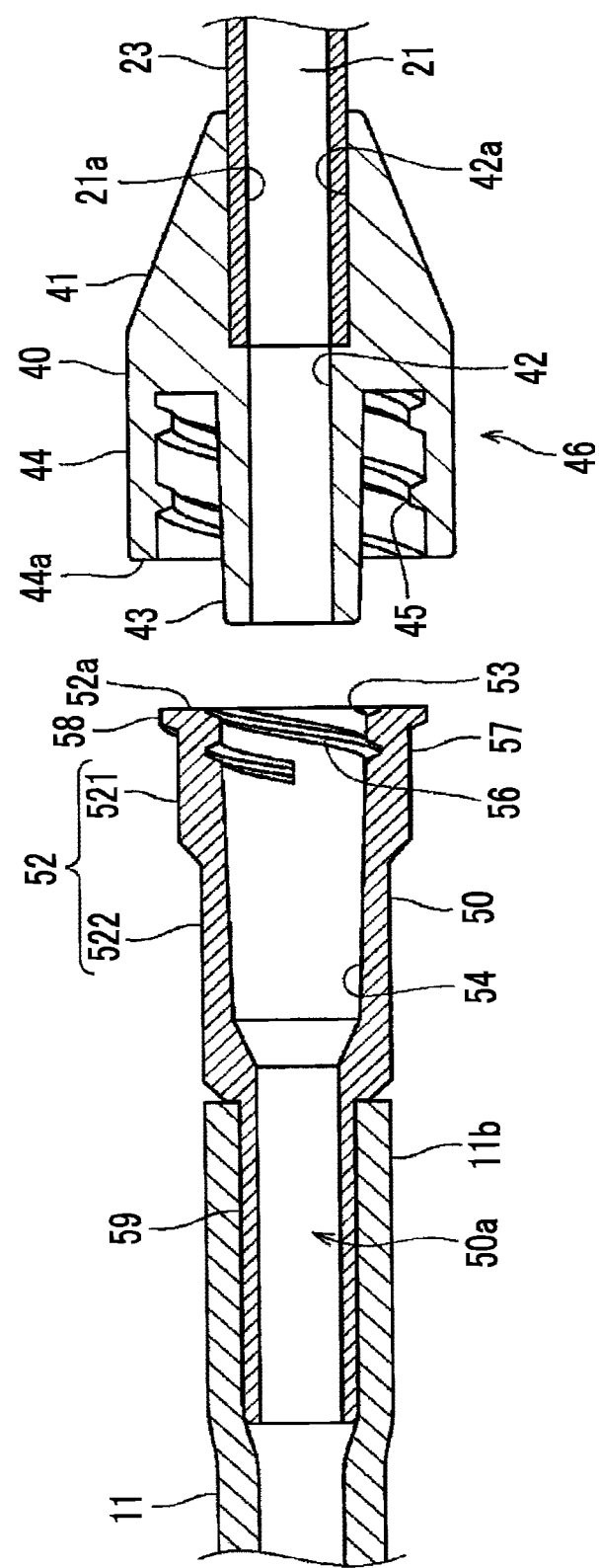
FIG. 5 is a cross-sectional view showing the flexible tube side connector (female connector) and a joint portion-side connector (male connector) of the coronary artery bypass surgery treatment tool according to Embodiment 1-1, and shows a state in which the flexible tube-side connector and the joint portion-side connector are separated from each other. Moreover.

As shown in FIG. 5, the male connector 40 includes a main body portion 41, a male luer 43 which protrudes from one end (a left end in FIG. 5) of the main body portion 41, and a tubular portion 44 which is disposed around the male luer 43 protruding from the one end of the main body portion 41.

The male luer 43 is formed in a tapered shape in which the male luer 43 is tapered toward a tip side (the left side in FIG. 5).

In addition, for example, the tip side of the male luer 43 protrudes further from a tip 44a of the tubular portion 44.

For example, a helical threaded portion 45 is formed on an inner peripheral surface of the tubular portion 44. That is, the tubular portion 44 has a female screw shape.

A through-hole 42 is formed in the male connector 40 from the other end (a right end in FIG. 5) of the main body portion 41 to a tip of the male luer 43.

For example, a portion on the other end side of the main body portion 41 in the through-hole 42 is a secondary tube-fixing portion 42a having a diameter smaller than that of a portion on the tip side of the male luer 43 in the through-hole 42.

The distal end of the secondary tube 23 is fixed to the male connector 40 by inserting the distal end of the secondary tube 23 into the secondary tube-fixing portion 42a.

Figure 3:
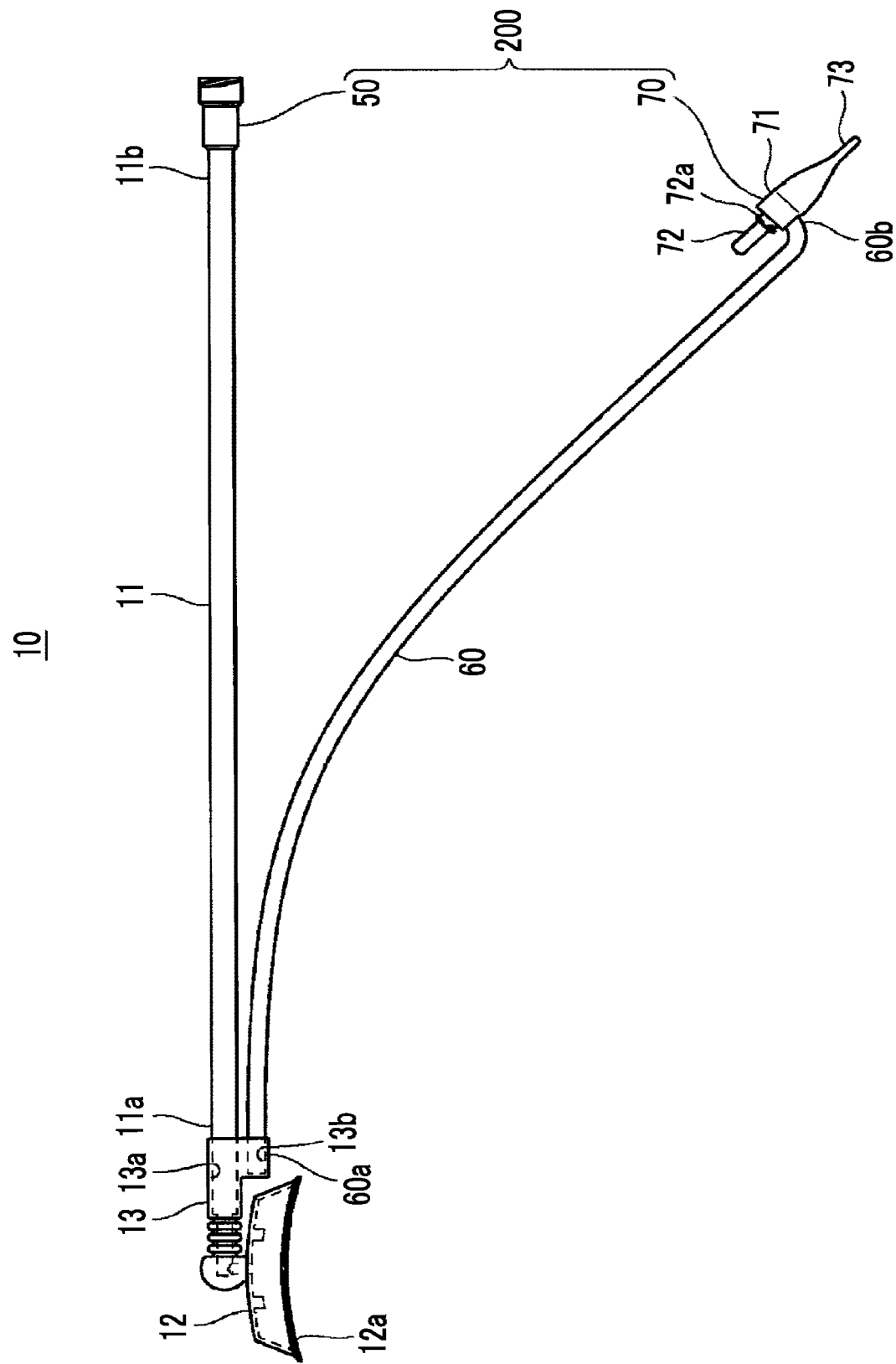
FIG. 3 is a schematic diagram of a treatment tool part (type 1) of the coronary artery bypass surgery treatment tool according to Embodiment 1-1. Moreover.

As shown in FIG. 3, for example, the treatment tool part 10 includes the flexible tube 11, the suction cup 12 which is provided at the distal end 11a of the flexible tube 11, and the female connector 50 which is provided at the proximal end 11b of the flexible tube 11.

The treatment tool part 10 further includes a flexible linear body 60 and a linear body-side connector 70.

For example, a connection member 13 is formed integrally with the suction cup 12.

A first insertion hole 13a and a second insertion hole 13b are formed in the connection member 13.

Although a shape of the connection member 13 is not particularly limited, for example, the connection member 13 is formed in a long shape on one side. Moreover, axial directions of the first insertion hole 13a and the second insertion hole 13b extend to be parallel in a longitudinal direction of the connection member 13.

Moreover, for example, opening directions of the first insertion hole 13a and the second insertion hole 13b are the same as each other.

The distal end 11a of the flexible tube 11 is inserted into the first insertion hole 13a, and thus, the distal end 11a is fixed. That is, the suction cup 12 is provided at the distal end 11a of the flexible tube 11 via the connection member 13.

One end side 60a of the linear body 60 is inserted into the second insertion hole 13b, and thus, the one end side 60a is fixed. That is, in the case of the present embodiment, the one end side 60a of the linear body 60 is fixed to the distal end 11a of the flexible tube 11 via the connection member 13 and is fixed to the suction cup 12 via the connection member 13.

However, the present invention is not limited to this example. That is, the one end side 60a of the linear body 60 may be directly fixed to the suction cup 12, and the one end side 60a of the linear body 60 may be directly fixed to the distal end 11a of the flexible tube 11.

In this way, the one end side 60a of the linear body 60 is fixed to the distal end 11a of the flexible tube 11 or the suction cup 12.

In addition, as described above, the opening directions of the first insertion hole 13a and the second insertion hole 13b are the same direction as each other. Accordingly, the flexible tube 11 and the linear body 60 are led out from the connection member 13 in the same direction as each other.

The suction cup 12 is formed in a bowl shape and has an opening portion 12a. In addition, it is preferable that an uneven shape be formed inside the suction cup 12 as necessary.

The opening portion 12a of the suction cup 12 communicates with an internal space of the flexible tube 11 through an internal space of the suction cup 12 and an internal space of the connection member 13.

In a state where the opening portion 12a of the suction cup 12 is applied to a heart of the living body, gas in the internal space of the suction cup 12 is sucked by the suction source 30 via the internal space of the connection member 13, the internal space of the flexible tube 11, an internal space (through-hole 50a in FIG. 6) of the female connector 50, an internal space (through-hole 42 in FIG. 6) of the male connector 40, the suction path 21 inside the joint portion 20, and the suction tube 31. Accordingly, the suction cup 12 adsorbs the heart. By holding the suction cup 12 at a desired position in this state, the heart can be maintained at the desired position.

Here, the linear body-side connector 70 will be described with reference to FIG. 7.

The linear body-side connector 70 is provided on the other end side 60b side of the linear body 60. The linear body-side connector 70 can be detachably connected to the female connector 50 (see FIG. 8).

That is, the treatment tool part 10 (therefore, the coronary artery bypass surgery treatment tool 100) includes the linear body 60 whose one end side 60a is fixed to the distal end 11a or the suction cup 12 of the flexible tube 11, the linear body-side connector 70 is provided on the other end side 60b of the linear body 60, and the linear body-side connector 70 can be detachably connected to the flexible tube-side connector (female connector 50) which is the connector provided at the proximal end 11b of the flexible tube 11, out of the male connector 40 and the female connector 50.

Figure 7:
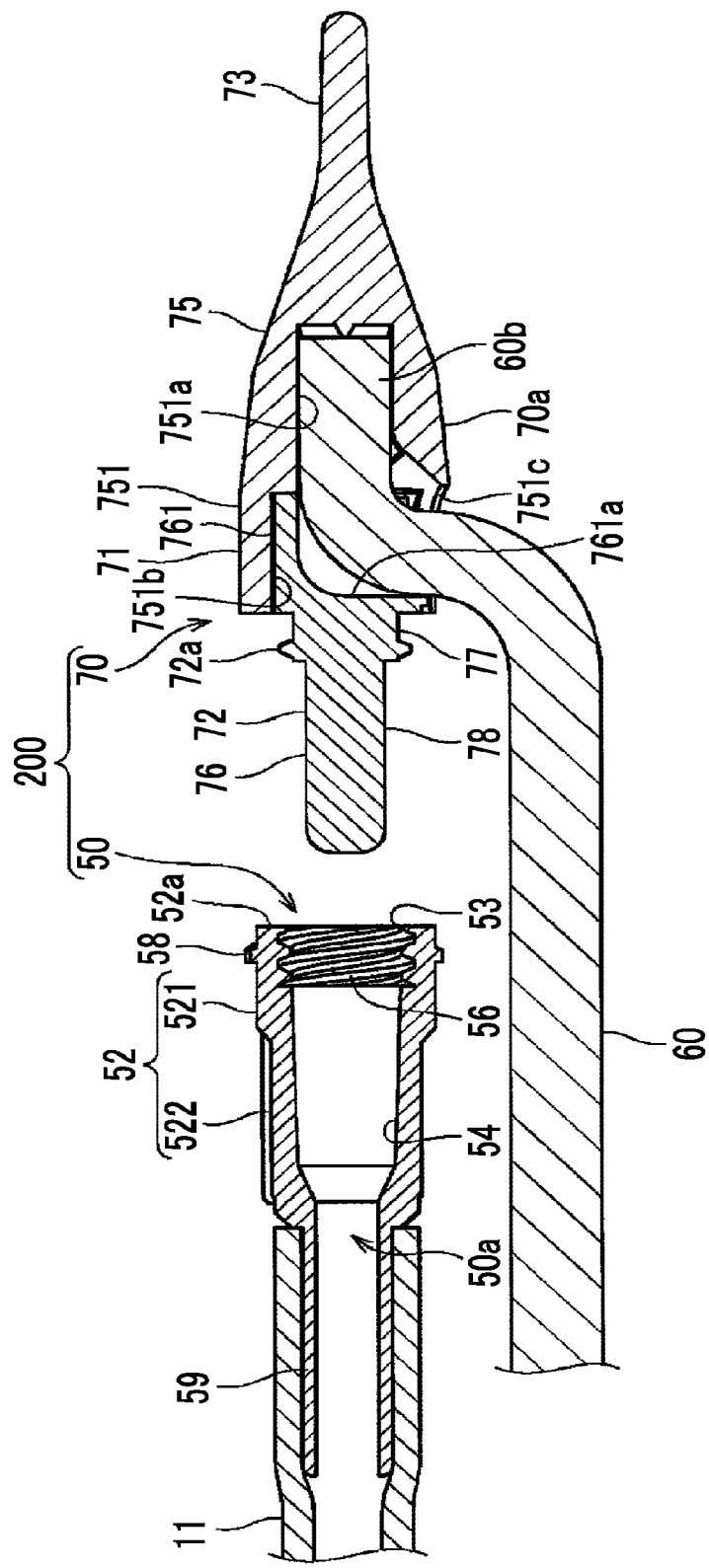
FIG. 7 is a cross-sectional view showing the flexible tube side connector (female connector) and a linear body-side connector (second male connector) of the coronary artery bypass surgery treatment tool according to Embodiment 1-1, and shows a state in which the flexible tube-side connector and the linear body-side connector are separated from each other. Moreover.

As shown in FIG. 7, the linear body 60 is led out from a peripheral surface 70a around an axis of the linear body-side connector 70.

The linear body-side connector 70 has a connection portion 72 which is disposed on one end side of the linear body-side connector 70 and is connected to the flexible tube-side connector (female connector 50), and a tapered protrusion portion 73 which is disposed on the other end side of the linear body-side connector 70.

Figure 8:
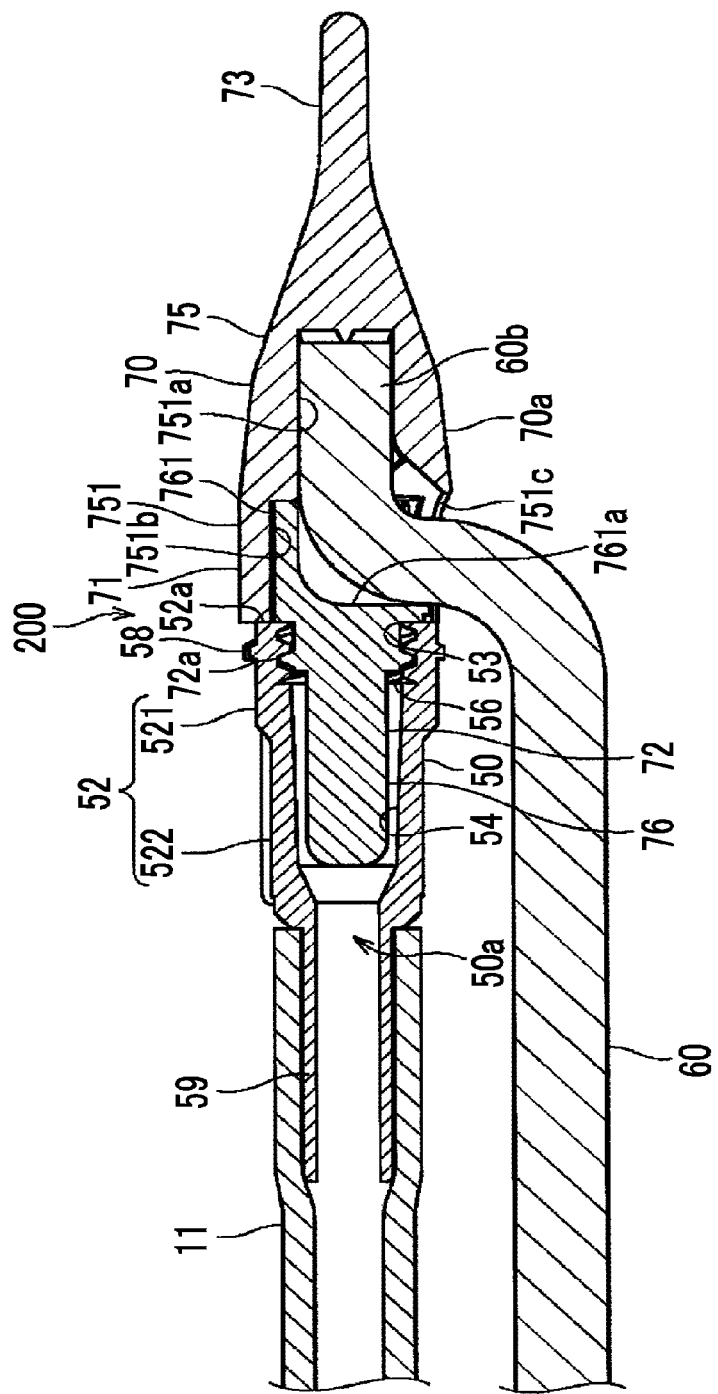
FIG. 8 is a cross-sectional view showing the flexible tube side connector (female connector) and the linear body-side connector (second male connector) of the coronary artery bypass surgery treatment tool according to Embodiment 1-1, and shows a state in which the flexible tube-side connector and the linear body-side connector are connected to each other. Moreover.

The linear body-side connector 70 includes a main body portion 71, and the connection portion 72 is a protrusion formed to protrude toward one side from the main body portion 71. The connection portion 72 is inserted into the female connector 50 as shown in FIG. 8. That is, the linear body-side connector 70 is a male connector (second male connector).

As described above, the flexible tube-side connector is the female connector 50, the linear body-side connector 70 is the second male connector which can be connected to the female connector 50, and the linear body-side connector 70 includes the main body portion 71 and the connection portion 72 which is a protrusion which is formed to protrude from the main body portion 71 and is inserted into the female connector 50.

Moreover, a protrusion direction of the protrusion portion 73 from the main body portion 71 and a protrusion direction of the connection portion 72 from the main body portion 71 are opposite to each other.

For example, the linear body-side connector 70 is configured by assembling two members such as a first member 75 and a second member 76 to each other.

The first member 75 is configured to include a main body component 751 and the above-described protrusion portion 73.

The main body component 751 is a tubular portion constituting the main body portion 71.

In the main body component 751, one end side is open and the other end side (protrusion portion 73 side) is closed.

In the main body component 751, a fixing hole 751a to which the other end side 60b of the linear body 60 is fixed, and a fitting hole 751b into which the second member 76 is fitted and fixed are formed.

The fixing hole 751a and the fitting hole 751b are disposed to be adjacent to each other and communicate with each other.

In the fixing hole 751a and the fitting hole 751b, the fitting hole 751b is disposed on an opening side of the main body component 751.

A cutout portion 751c is formed on an outer peripheral wall of a portion of the main body component 751 where the fitting hole 751b is formed.

The second member 76 includes a fitting portion 761 which is fitted into the fitting hole 751b of the first member 75 and the above-described connection portion 72.

A recessed portion 761a is formed in the fitting portion 761.

The recessed portion 761a communicates with the fixing hole 751a and also communicates with the cutout portion 751c.

The linear body 60 having the other end side 60b fixed to the fixing hole 751a is led out (extracted) from the peripheral surface 70a of the linear body-side connector 70 via the inside of the recessed portion 761a and the cutout portion 751c.

The connection portion 72 protrudes from the fitting portion 761 to one side.

An engaging convex portion 72a is formed on the outer peripheral surface of the connection portion 72.

More specifically, the connection portion 72 includes a columnar large-diameter portion 77 and a columnar small-diameter portion 78 having a diameter smaller than the large-diameter portion 77. The large-diameter portion 77 and the small-diameter portion 78 are disposed coaxially with each other and are connected to each other in the axial direction.

The fitting portion 761 is provided at an end portion of the large-diameter portion 77 opposite to the small-diameter portion 78 side.

The engaging convex portion 72a is formed on the outer peripheral surface of the large-diameter portion 77.

Figure 10:
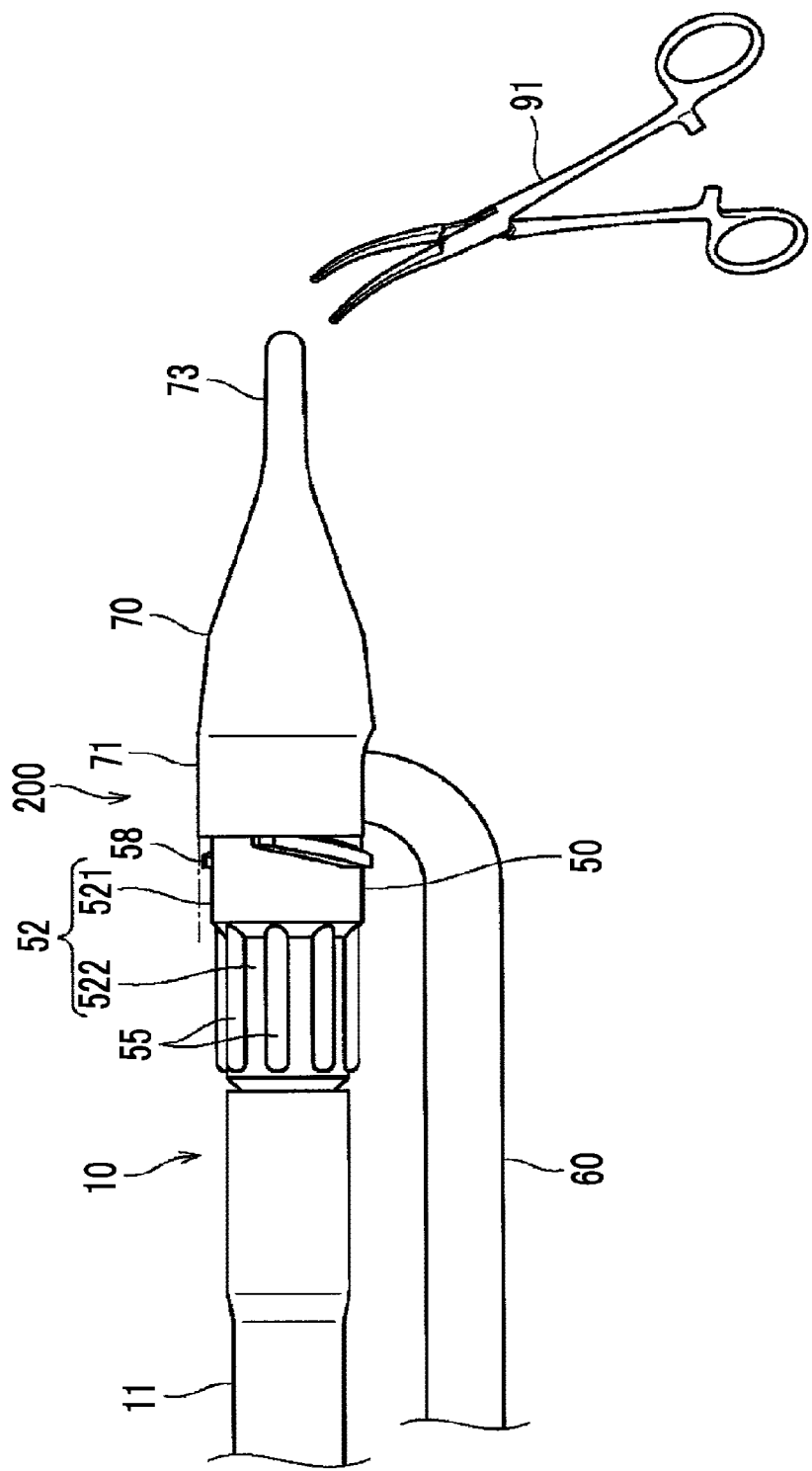
FIG. 10 is a schematic view showing a state in which grasping of a protrusion portion of the linear body side connector (second male connector) of the coronary artery bypass surgery treatment tool according to Embodiment 1-1 is attempted with forceps. Moreover.

Here, as shown in FIG. 10, during a treatment using the coronary artery bypass surgery treatment tool 100, it is possible to grasp the protrusion portion 73 of the linear body-side connector 70 by forceps 91 and pull the treatment tool part 10.

Next, the female connector 50 will be described with reference to FIGS. 4(a), 4(b), and 4(c).

The female connector 50 is formed in a tubular shape as a whole. That is, the through-hole 50a (FIG. 4(c)) is formed from one end of the female connector 50 to the other end thereof.

A portion of the female connector 50 in an axial direction (axial direction of the through-hole 50a) of the female connector 50 constitutes an accommodation portion 52, and the remaining portion constitutes an insertion tubular portion 59.

An opening 53 is formed at one end 52a of the accommodation portion 52. The connection portion 72 of the linear body-side connector 70 is inserted into the accommodation portion 52 from the opening 53.

A helical engaging recessed portion 56 (spiral groove) is formed on an inner peripheral surface 54 of the accommodation portion 52.

The engaging recessed portion 56 of the accommodation portion 52 and the engaging convex portion 72a of the connection portion 72 are screwed to each other, and thus, the female connector 50 and the linear body-side connector 70 are detachably connected to each other.

However, the present invention is not limited to this example. That is, the engaging convex portion 72a may be formed on the inner peripheral surface 54 of the accommodation portion 52 while the engaging recessed portion 56 may be formed on the outer peripheral surface of the connection portion 72, the engaging recessed portion 56 and the engaging convex portion 72a are screwed to each other, and thus, the female connector 50 and the linear body-side connector 70 may be connected to each other.

As described above, the female connector 50 has the hollow accommodation portion 52 which has the opening 53 at one end 52a and into which the connection portion 72 is inserted from the opening 53. The engaging convex portion 72a is formed on one of the outer peripheral surface of the connection portion 72 and the inner peripheral surface 54 of the accommodation portion 52, the helical engaging recessed portion 56 is formed on the other thereof, the engaging convex portion 72a and the engaging recessed portion 56 are screwed to each other, and thus, the linear body-side connector 70 and the female connector 50 are detachably connected to each other.

Moreover, in the case of the present embodiment, the engaging convex portion 72a is formed on the outer peripheral surface of the connection portion 72, and the engaging recessed portion 56 is formed on the inner peripheral surface 54 of the accommodation portion 52.

The accommodation portion 52 is a female luer in which an inner diameter of the accommodation portion 52 decreases in a depth direction from the opening 53. That is, the inner diameter of the accommodation portion 52 gradually decreases toward the left side in FIG. 5.

In addition, a second engaging convex portion 58 is formed in the vicinity of the one end 52a of the accommodation portion 52 on an outer peripheral surface of the accommodation portion 52.

Further, as described above, the male connector 40 is provided at the distal end 21a of the suction path 21 of the joint portion 20.

The male luer 43 (FIG. 5) of the male connector 40 is formed in a shape which is fitted to the accommodation portion 52. The threaded portion 45 formed on the peripheral surface of the tubular portion 44 of the male connector 40 is screwed to the second engaging convex portion 58 of the accommodation portion 52. That is, the male connector 40 has a male luer lock structure 46 which includes the male luer 43 which is fitted to the female luer (accommodation portion 52), the tubular portion 44 which is provided around the male luer 43, and the threaded portion 45 which is formed on the inner peripheral surface of the tubular portion 44 and is screwed to the second engaging convex portion 58 of the accommodation portion 52.

More specifically, the accommodation portion 52 includes a large-diameter portion 521 including one end 52a and a small-diameter portion 522. An outer peripheral surface of the small-diameter portion 522 is formed to have a diameter smaller than an outer peripheral surface of the large-diameter portion 521.

The large-diameter portion 521 and the small-diameter portion 522 are disposed coaxially with each other and are connected to each other in an axial direction.

Moreover, the second engaging convex portion 58 is formed on the outer peripheral surface of the large-diameter portion 521.

For example, the outer peripheral surface of the insertion tubular portion 59 is formed to have a diameter smaller than the outer peripheral surface of the small-diameter portion 522.

Moreover, for example, as shown in FIG. 10, a plurality of ribs 55 extending in the axial direction of the accommodation portion 52 may be formed on the outer peripheral surface of the small-diameter portion 522. In this case, since the ribs 55 prevent slipping, an operation of screwing the female connector 50 and the linear body-side connector 70 to each other can be performed more easily.

Moreover, the position at which the second engaging convex portion 58 is formed on the outer peripheral surface of the accommodation portion 52 of the female connector 50 may be separated from the one end 52a as in the examples shown in FIGS. 7, 8, and 10, or may be adjacent to one end 52a as in the examples shown in FIGS. 4(a), 4(b), 4(c), 5, and 6. In any case, the female connector 50 is formed so as to be connectable to both the male connector 40 and the linear body-side connector 70.

As shown in FIG. 5, the insertion tubular portion 59 is inserted into the proximal end 11b of the flexible tube 11, and thus, the female connector 50 is attached to the proximal end 11b of the flexible tube 11.

The female connector 50 can be selectively detachably connected to one of the male connector 40 and the linear body-side connector 70.

Figure 6:
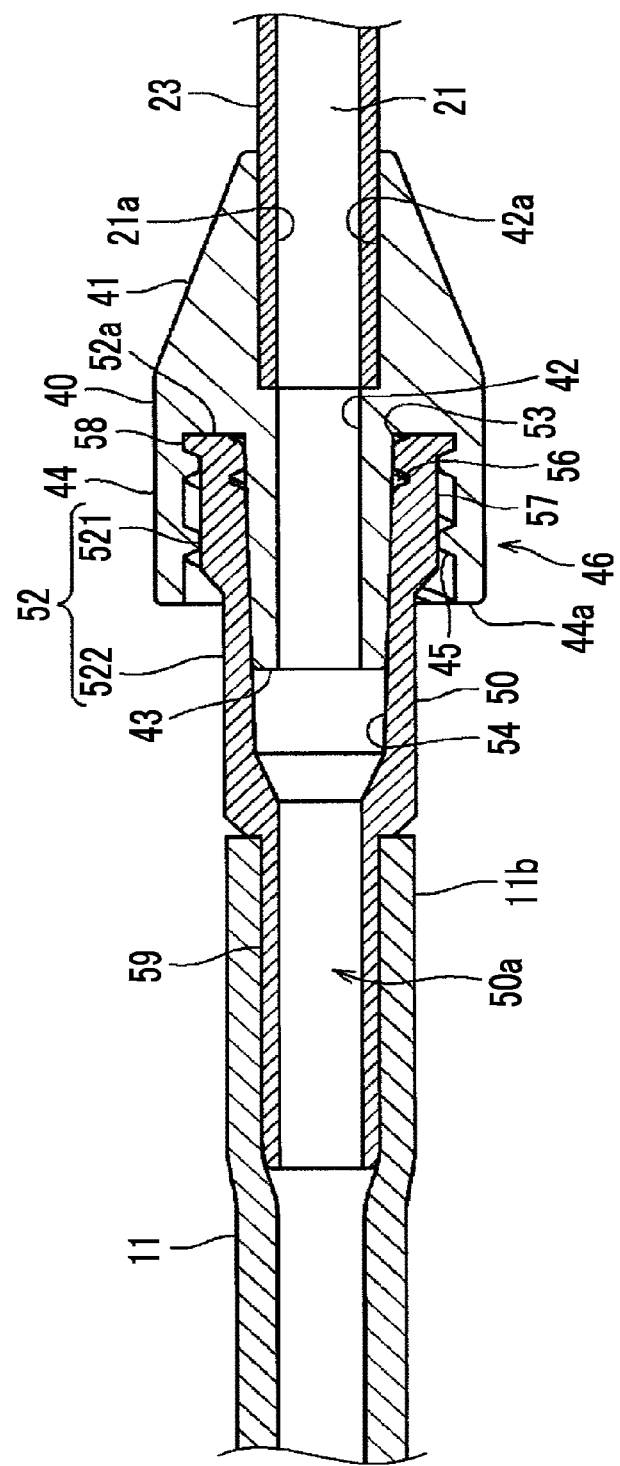
FIG. 6 is a cross-sectional view showing the flexible tube side connector (female connector) and the joint portion-side connector (male connector) of the coronary artery bypass surgery treatment tool according to Embodiment 1-1, and shows a state in which the flexible tube-side connector and the joint portion-side connector are connected to each other. Moreover.

That is, as shown in FIG. 6, the male luer 43 is inserted into the accommodation portion 52 and the threaded portion 45 and the second engaging convex portion 58 are screwed to each other. Accordingly, the female connector 50 and the male connector 40 can be connected to each other. In a state where the female connector 50 and the male connector 40 are connected to each other, the male luer 43 and the accommodation portion 52 are fitted to each other and are in close contact with each other.

Further, as shown in FIG. 8, the connection portion 72 is inserted into the accommodation portion 52 and the engaging convex portion 72a and the engaging recessed portion 56 are screwed to each other. Accordingly, the female connector 50 and the linear body-side connector 70 can be connected to each other. Moreover, in a state where the female connector 50 and the linear body-side connector 70 are connected to each other, for example, the connection portion 72 and the accommodation portion 52 are not in a fitted state and are not in close contact with each other.

As can be seen from the above descriptions, the treatment tool part 10 includes the flexible tube 11, the suction cup 12 which has the opening portion 12a formed to communicate with the flexible tube 11 and is provided at one end (distal end 11a) of the flexible tube 11, the linear body 60 which has the one end side 60a fixed to the one end of the flexible tube 11 or the suction cup 12, and the female connector 50 which has the hollow accommodation portion 52 and is provided on the other end (proximal end 11b) of the flexible tube 11.

Moreover, the accommodation portion 52 is a female luer which has the opening 53 at the one end 52a and in which the inner diameter of the accommodation portion 52 decreases in the depth direction from the opening 53, and the spiral groove (engaging recessed portion 56) is formed on the inner peripheral surface 54 of the female luer.

Further, the linear body-side connector 70 which can be connected to the female connector 50 is provided on the other end side 60b of the linear body 60, the linear body-side connector 70 includes the main body portion 71 and the connection portion 72 which is the protrusion which is formed to protrude from the main body portion 71 and is inserted into the accommodation portion 52, and the engaging convex portion 72a which is screwed to the spiral groove (engaging recessed portion 56) is formed on the outer peripheral surface of the connection portion 72.

Here, an example of a material of each component of the coronary artery bypass surgery treatment tool 100 will be described.

For example, the secondary tube 23, the flexible tube 11, and the linear body 60 are made of a soft resin, have flexibility, and can be bent flexibly.

For example, the suction cup 12 is made of a soft resin.

For example, each of the three-way valve 24, the male connector 40, and the female connector 50 is made of a hard resin.

For example, the connection member 13 is made of a resin (hard resin or soft resin).

For example, the first member 75 of the linear body-side connector 70 is made of a resin (hard resin or soft resin).

For example, the second member 76 of the linear body-side connector 70 is made of a resin (hard resin or soft resin).

Here, in the case of the treatment tool part 10 (type 1) shown in FIG. 3, the connection member 13 is formed to be long on one side. Further, the suction cup 12 is also formed to be long on one side, and the suction cup 12 is disposed along the longitudinal direction of the connection member 13.

Figure 9:
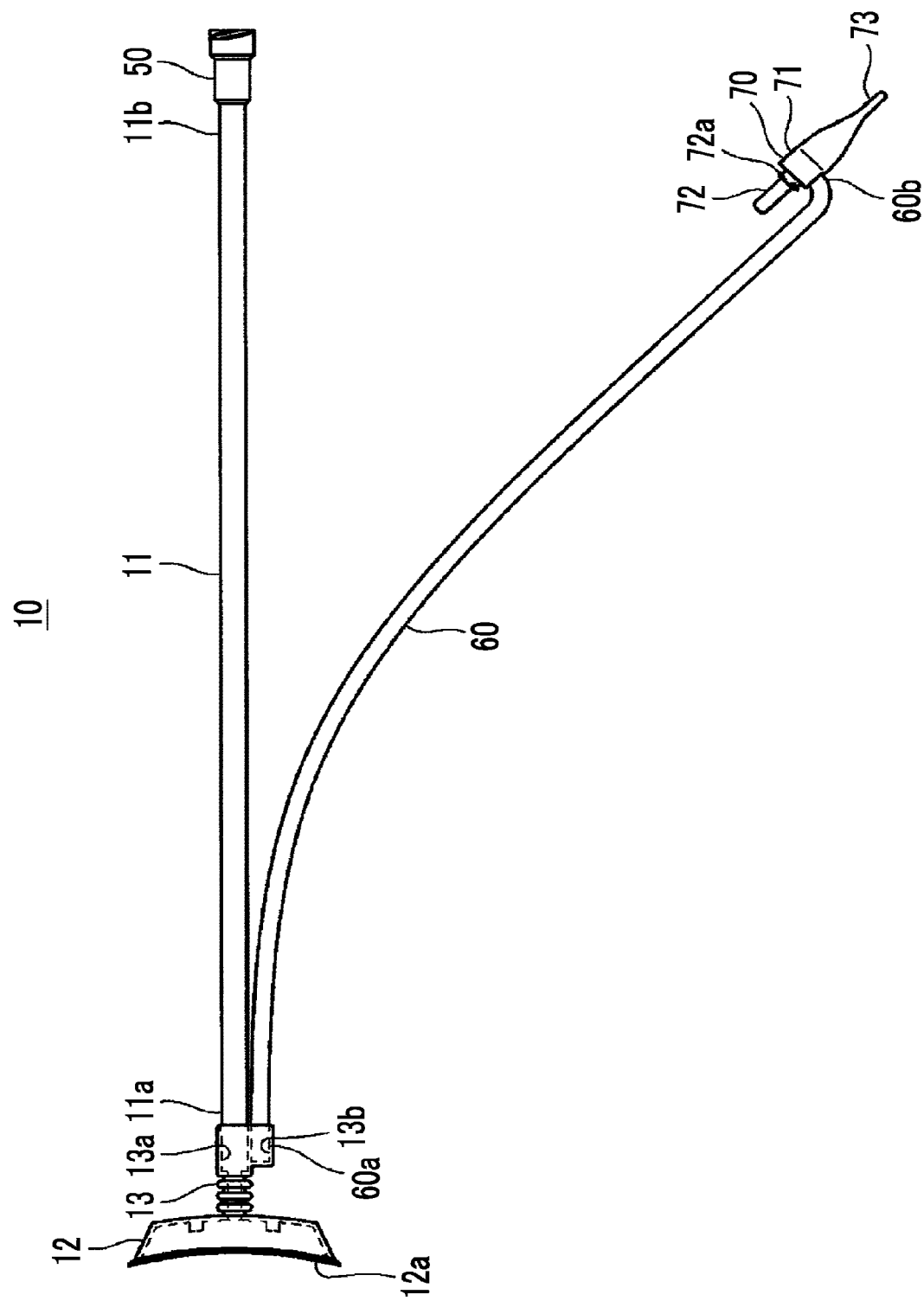
FIG. 9 is a schematic diagram of a treatment tool part (type 2) of the coronary artery bypass surgery treatment tool according to Embodiment 1-1.

Meanwhile, a type 2 shown in FIG. 9 can also be used as the treatment tool part 10. In the case of the treatment tool part 10 shown in FIG. 9, the longitudinal direction of the suction cup 12 is disposed to be orthogonal to the longitudinal direction of the connection member 13.

Moreover, a plurality of treatment tool parts 10 and one joint portion 20 can be provided as a set (kit). In this case, for example, a set including the treatment tool part 10 of the type 1 shown in FIG. 3 and the treatment tool part 10 of the type 2 shown in FIG. 9 can be provided.

Accordingly, it is possible to select and use the treatment tool part 10 suitable for a practitioner's preference or suitable for a necessary treatment, out of the type 1 and type 2 of the treatment tool part 10.

Next, an example of the treatment using the coronary artery bypass surgery treatment tool 100 will be described with reference to FIGS. 11, 12(a), and 12(b).

Figure 11:
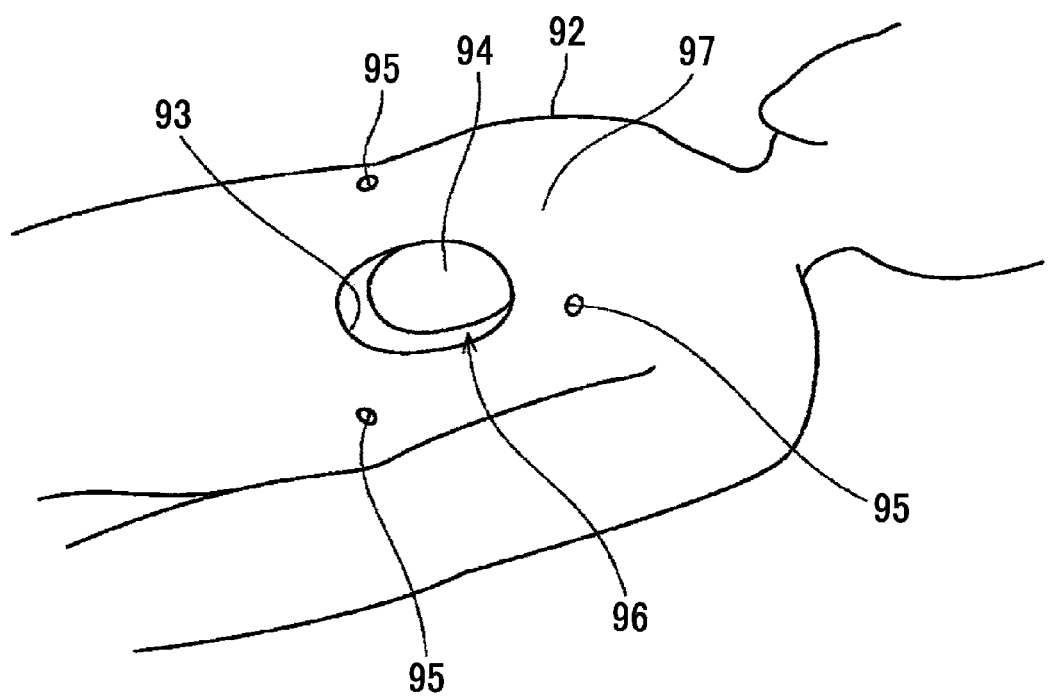
FIG. 11 is a schematic diagram explaining an example of a treatment using the coronary artery bypass surgery treatment tool according to Embodiment 1-1. Moreover.

As shown in FIG. 11, the incision 93 which is an opening reaching the thoracic cavity 96 is formed on a chest wall 97 of a subject 92 such as a human body, and a heart 94 is exposed to the outside.

Meanwhile, the plurality of small incision holes 95 smaller than the incision 93 are formed in a portion around the incision 93 in the chest wall 97. The number of small incision holes 95 can be equal to the number of treatment tool parts 10 included in the coronary artery bypass surgery treatment tool 100, and in the present embodiment, for example, the number of the small incision holes is three.

Moreover, an indwelling sheath (not shown) may be provided in each small incision hole 95.

Next, in the treatment tool part 10 which is separated from the joint portion 20 and in which the female connector 50 and the linear body-side connector 70 are connected to each other, the female connector 50 and the linear body-side connector 70 of the treatment tool part 10 are disposed in the vicinity of the small incision hole 95 in the thoracic cavity 96.

Next, as shown in FIG. 12(a), a tip side of the forceps 91 is inserted into the thoracic cavity 96 via the small incision hole 95 from the outside of the subject 92, and the protrusion portion 73 of the linear body-side connector 70 of the treatment tool part 10 is grasped by the forceps 91.

Moreover, by pulling the forceps 91, the linear body-side connector 70 and the female connector 50, and a portion of the linear body 60 and a portion of the flexible tube 11 are extracted from the thoracic cavity 96 through the small incision hole 95. In addition, in this state, the suction cup 12 and a portion of the connection member 13 side in the treatment tool part 10 are located in the thoracic cavity 96.

Moreover, as shown in FIG. 12(b), the suction cup 12 is disposed in the vicinity of a desired adsorption site of the heart 94.

Further, the linear body-side connector 70 is separated from the female connector 50.

Moreover, the female connector 50 is connected to the joint portion-side connector 40 of the joint portion 20 outside the subject 92.

This operation is repeated for each treatment tool part 10.

As a result, each treatment tool part 10 is connected to each male connector 40 of the joint portion 20 (see FIG. 1).

Thereafter, the suction cup 12 of each treatment tool part 10 is applied to a desired adsorption site of the heart 94, the suction source 30 is activated, and each suction cup 12 is adsorbed to the heart 94.

In this way, the heart 94 can be held at a desired position.

Thereafter, coronary artery bypass surgery can be performed.

Here, since each treatment tool part 10 can be separated from the joint portion 20, each treatment tool part 10 can be handled individually. Further, each treatment tool part 10 is inserted into the thoracic cavity 96 from the female connector 50 and the portion on the linear body-side connector 70 side, the linear body-side connector 70, the female connector 50, the linear body 60, and the flexible tube 11 are extracted from the thoracic cavity 96 via each small incision hole 95 using the forceps 91 or the like, and thereafter, the treatment tool part 10 can be connected to the joint portion 20.

Accordingly, the female connector 50, the linear body-side connector 70, a portion of the flexible tube 11, and a portion of the linear body 60 of each treatment tool part 10 can be extracted from each corresponding small incision hole 95.

Therefore, during the operation of disposing each suction cup 12 at a desired position and the subsequent coronary artery bypass surgery, the flexible tube 11 and the linear body 60 can be kept out of the way.

Accordingly, even if the incision 93 is made more compact than the related art, the coronary artery bypass surgery and a preparation thereof (disposition of the suction cup 12, or the like) can be suitably performed.

According to the first embodiment as described above, the flexible tube 11 and the joint portion 20 are detachable.

For this reason, handling properties of the coronary artery bypass surgery treatment tool 100 are excellent.

For example, the flexible tube 11 removed from the joint portion 20 is inserted into the thoracic cavity 96 (FIG. 11) from the incision 93 (FIG. 11), the flexible tube 11 is extracted from the small incision hole 95 (FIGS. 12(a) and 12(b)), and the flexible tube 11 can be connected to the joint portion 20.

Therefore, it is possible to easily perform an operation of extracting the female connector 50, the linear body-side connector 70, a portion of the flexible tube 11, and a portion of the linear body 60 of each treatment tool part 10 from each corresponding small incision hole 95.

Thereby, since the incision 93 can be reduced, it is possible to reduce the burden on the living body.

Further, since the linear body 60 is led out from the peripheral surface 70a around an axis of the linear body-side connector 70, the flexible tube 11 and the linear body 60 can be easily arranged in parallel with each other as shown in FIG. 8. Therefore, it is possible to reduce a resistance when the treatment tool part 10 is extracted from the thoracic cavity 96 as shown in FIG. 12(b).

Moreover, since the linear body-side connector 70 includes the protrusion portion 73 disposed on the other end side of the linear body-side connector 70, the protrusion portion 73 is grasped by the forceps 91 or the like, and thus, handling (for example, the operation of extracting the treatment tool part 10 from the thoracic cavity 96 as shown in FIG. 12(a)) of the treatment tool part 10 can be easily performed.

Further, since the protrusion portion 73 has a tapered shape, it is possible to reduce the resistance when the treatment tool part 10 is extracted from the thoracic cavity 96 as shown in FIG. 12(b).

Moreover, the engaging convex portion 72a is formed on the outer peripheral surface of the connection portion 72 of the linear body-side connector 70, the engaging recessed portion 56 is formed on the inner peripheral surface 54 of the accommodation portion 52 of the female connector 50, the engaging convex portion 72a and the engaging recessed portion 56 are screwed to each other, and thus, the linear body-side connector 70 and the female connector 50 are detachably connected to each other.

Therefore, the connection portion 72 of the linear body-side connector 70 can be made more compact than the male luer lock structure 46 of the male connector 40. That is, at least an outer diameter of the connection portion 72 can be made smaller than an outer diameter (an outer diameter of the tubular portion 44) of the male luer lock structure 46.

Further, since the treatment tool part 10 can be handled by grasping the protrusion portion 73 with the forceps 91, it is not necessary to grasp the linear body 60 or the flexible tube 11, and damage to the linear body 60 or the flexible tube 11 can be suppressed.

Embodiment 1-2

Next, Embodiment 1-2 will be described with reference to FIGS. 13 to 16.

A treatment tool part 10 (FIG. 13) according to the present embodiment is different from the treatment tool part 10 (the treatment tool part shown in FIG. 3 or the treatment tool part 10 shown in FIG. 9) according to Embodiment 1-1 as described below, and is configured similarly to the treatment tool part 10 according to Embodiment 1-1 in other respects.

Figure 13:
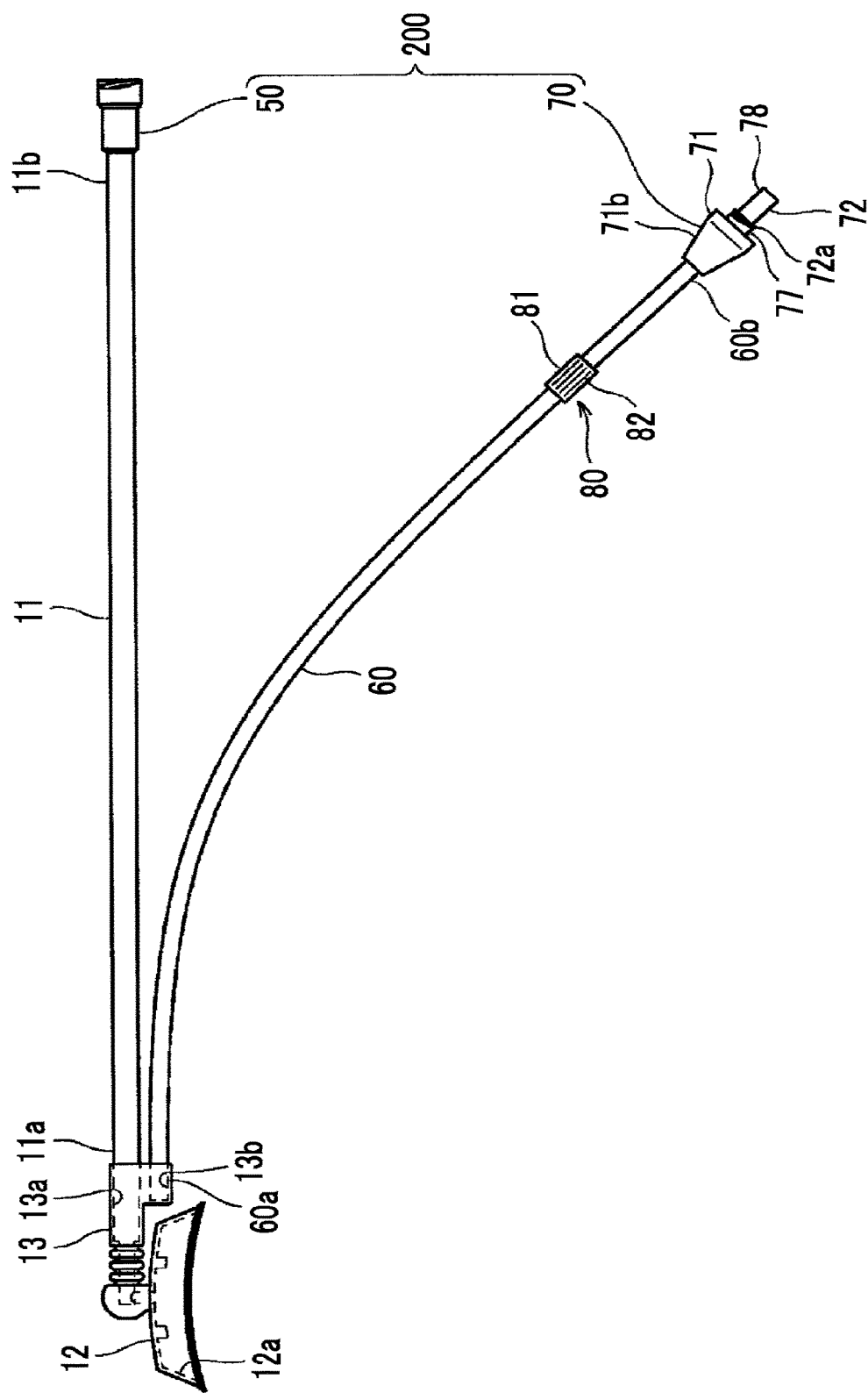
FIG. 13 is a schematic view of a treatment tool part of a coronary artery bypass surgery treatment tool according to Embodiment 1-2. Moreover.

As shown in FIG. 13, compared to the treatment tool part 10 (FIG. 3 or FIG. 9) according to Embodiment 1-1, in the treatment tool part 10 according to the present embodiment, a structure of the linear body-side connector 70 is different.

Figure 14:
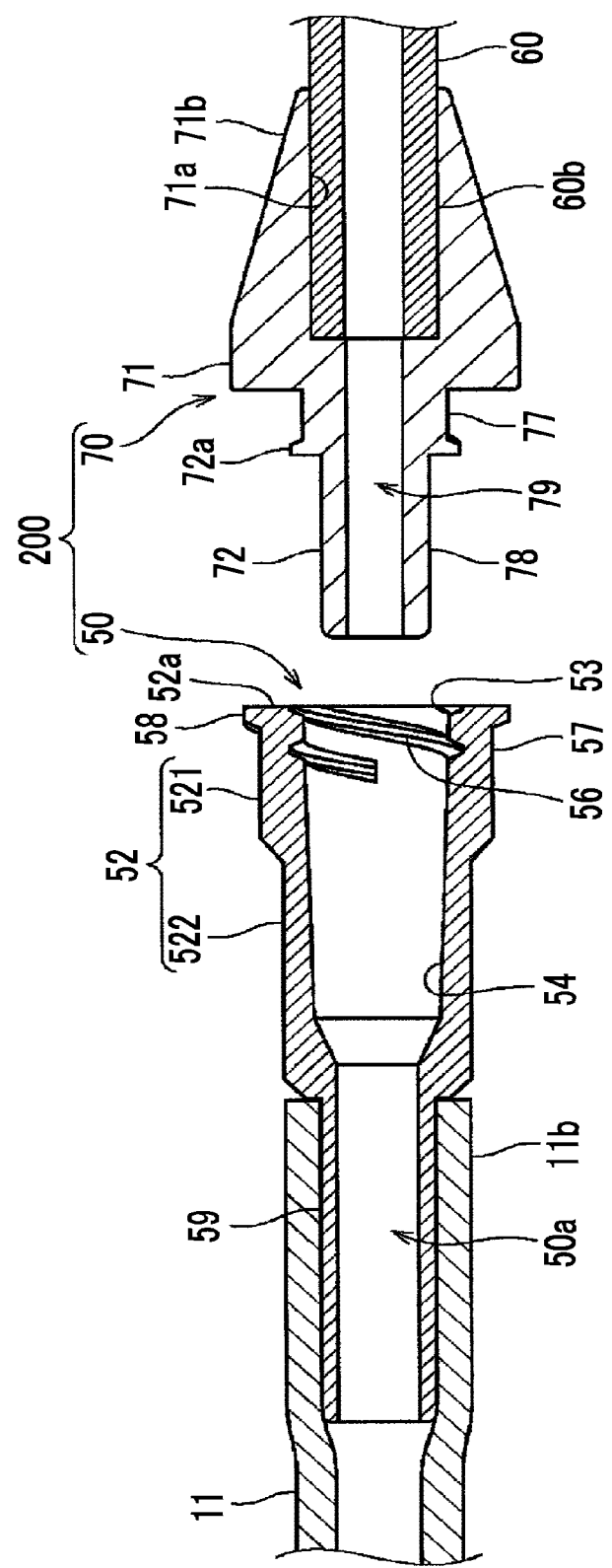
FIG. 14 is a cross-sectional view showing a flexible tube side connector (female connector) and a linear body-side connector (second male connector) of the coronary artery bypass surgery treatment tool according to Embodiment 1-2, and shows a state in which the flexible tube-side connector and the linear body-side connector are separated from each other. Moreover.

As shown in FIG. 14, in a case of the present embodiment, the linear body-side connector 70 includes a main body portion 71 and a connection portion 72 which protrudes from one end of the main body portion 71.

Similarly to Embodiment 1-1, the connection portion 72 is a portion which is connected to a female connector 50.

Similarly to Embodiment 1-1, an engaging convex portion 72a is formed on an outer peripheral surface of the connection portion 72.

Figure 15:
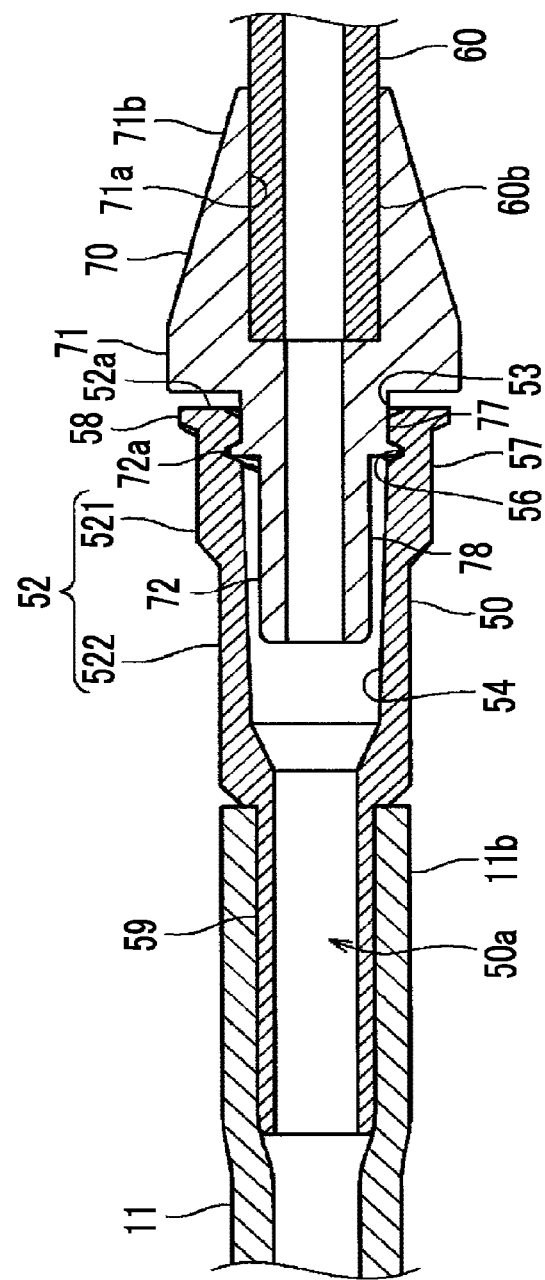
FIG. 15 is a cross-sectional view showing the flexible tube side connector (female connector) and the linear body-side connector (second male connector) of the coronary artery bypass surgery treatment tool according to Embodiment 1-2, and shows a state in which the flexible tube-side connector and the linear body-side connector are connected to each other.

Also in the present embodiment, as shown in FIG. 15, the female connector 50 and the linear body-side connector 70 can be connected to each other.

Moreover, similarly to Embodiment 1-1 the connection portion 72 has a large-diameter portion 77 and a small-diameter portion 78, and an engaging convex portion 72a is formed on the outer peripheral surface of the large-diameter portion 77.

A fixing hole 71a for fitting and fixing the other end side 60b of the linear body 60 is formed inside the main body portion 71.

Here, in the present embodiment, an example in which a through-hole is formed between both ends of the linear body-side connector 70 is shown. However, the present invention is not limited to this example, and a portion (insertion protrusion 72 or the like) of the linear body-side connector 70 except for the fixing hole 71a may be a non-hollow structure, that is, a solid structure.

An outer peripheral surface of the main body portion 71 includes a tapered surface 71b which decreases in diameter toward the other end side (side opposite to the connection portion 72 side) of the main body portion 71.

In the case of the present embodiment, the linear body 60 is led out from a side opposite to the connection portion 72 side in the main body portion 71.

In this way, in a case of the present embodiment, the linear body-side connector 70 has the connection portion 72 which is disposed on one end side of the linear body-side connector 70 and is connected to the flexible tube-side connector (female connector 50), and the linear body 60 is led out from the other end side of the linear body-side connector 70.

Figure 16:
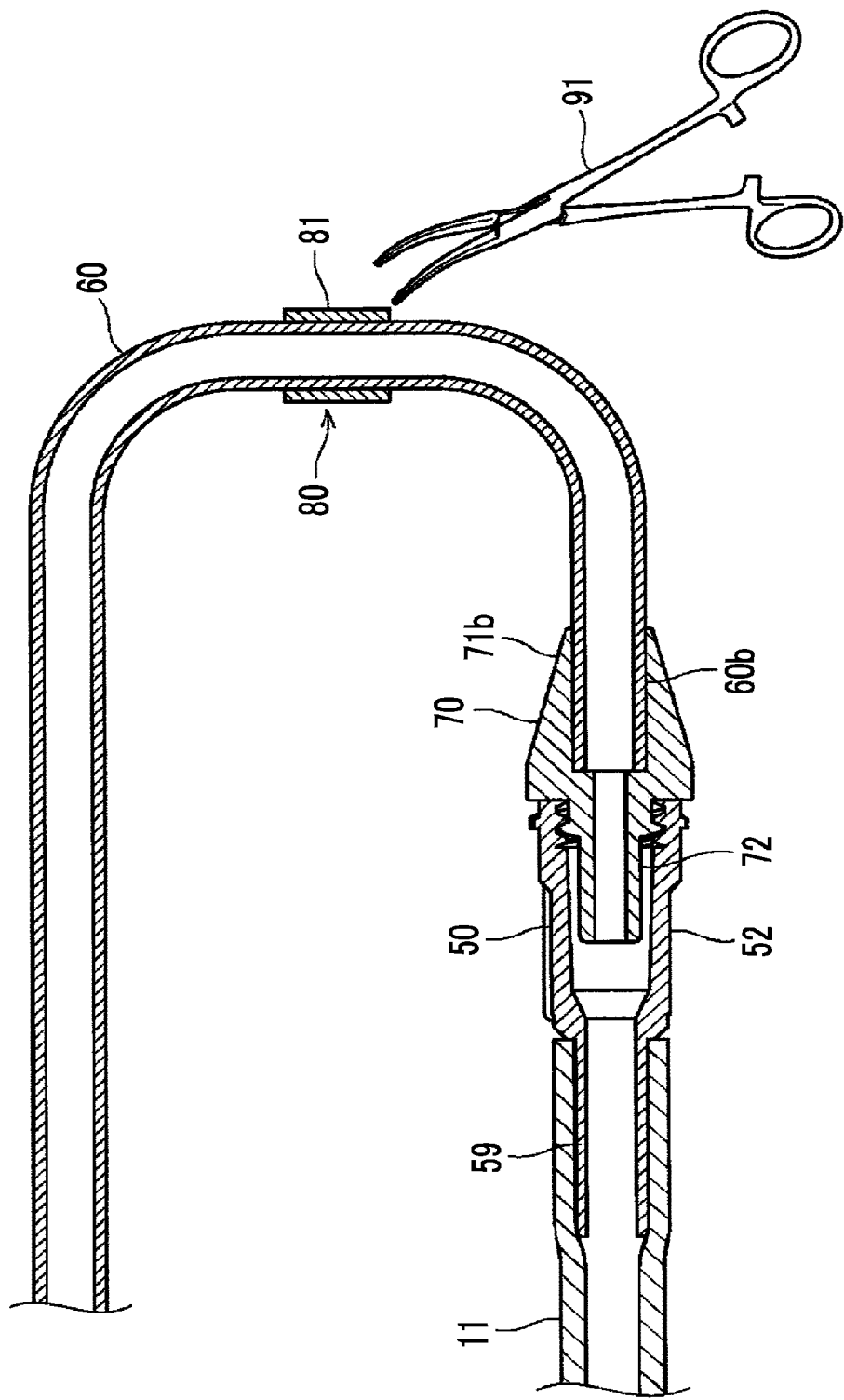
FIG. 16 is a schematic view showing a state in which grasping of a reinforcing portion of a linear body of the coronary artery bypass surgery treatment tool according to Embodiment 1-2 is attempted with forceps.

In the case of the present embodiment, as shown in FIGS. 13 and 16, a reinforcing portion 80 which is reinforced more than the other portions of the linear body 60 is formed in a portion of the linear body 60 near the linear body-side connector 70.

For example, the reinforcing portion 80 is configured by a reinforcing tube 81 being externally fitted around the linear body 60.

In the case of the present embodiment, when the treatment tool part 10 is extracted from the thoracic cavity, the reinforcing portion 80 can be grasped by forceps 91 as shown in FIG. 16.

In addition, for example, a plurality of grooves 82 extending in an axial direction of the reinforcing tube 81 are formed on an outer peripheral surface of the reinforcing tube 81. Accordingly, it is possible to prevent the forceps 91 from slipping from the reinforcing tube 81 when the reinforcing tube 81 is grasped by the forceps 91.

In addition, a coronary artery bypass surgery treatment tool (the entire tool is not shown) according to the present embodiment is different from the coronary artery bypass surgery treatment tool 100 according to Embodiment 1-1 in that the treatment tool part 10 shown in FIG. 13 is provided instead of the treatment tool part 10 shown in FIG. 3 or FIG. 9, and the coronary artery bypass surgery treatment tool according to the present embodiment is configured similarly to the coronary artery bypass surgery treatment tool 100 according to Embodiment 1-1 in other respects.

In the case of the present embodiment, the treatment tool part 10 can be handled by grasping the reinforcing portion 80 with the forceps 91. Accordingly, there is no need to directly grasp the linear body 60 or the flexible tube 11, and thus, damage to the linear body 60 or the flexible tube 11 can be suppressed.

Moreover, since the outer peripheral surface of the main body portion 71 of the linear body-side connector 70 has the tapered surface 71b, it is possible to reduce a resistance when the treatment tool part 10 is extracted from the thoracic cavity.

Hereinbefore, the embodiments are described with reference to the drawings. However, the embodiments are examples of the present invention, and thus, various configurations other than the above-described embodiments can also be adopted.

For example, in each of the above-described embodiments, the example is described in which the female connector 50 is provided at the proximal end 11b of the flexible tube 11 while the male connector 40 is provided at the distal end 21a of the suction path 21 of the joint portion 20. However, contrary to this example, the male connector 40 may be provided at the proximal end 11b of the flexible tube 11 while the female connector 50 may be provided at the distal end 21a of the suction path 21 of the joint portion 20.

In this case, the linear body-side connector 70 is a female connector (second female connector) which can be connected to the male connector 40.

Figure 17:
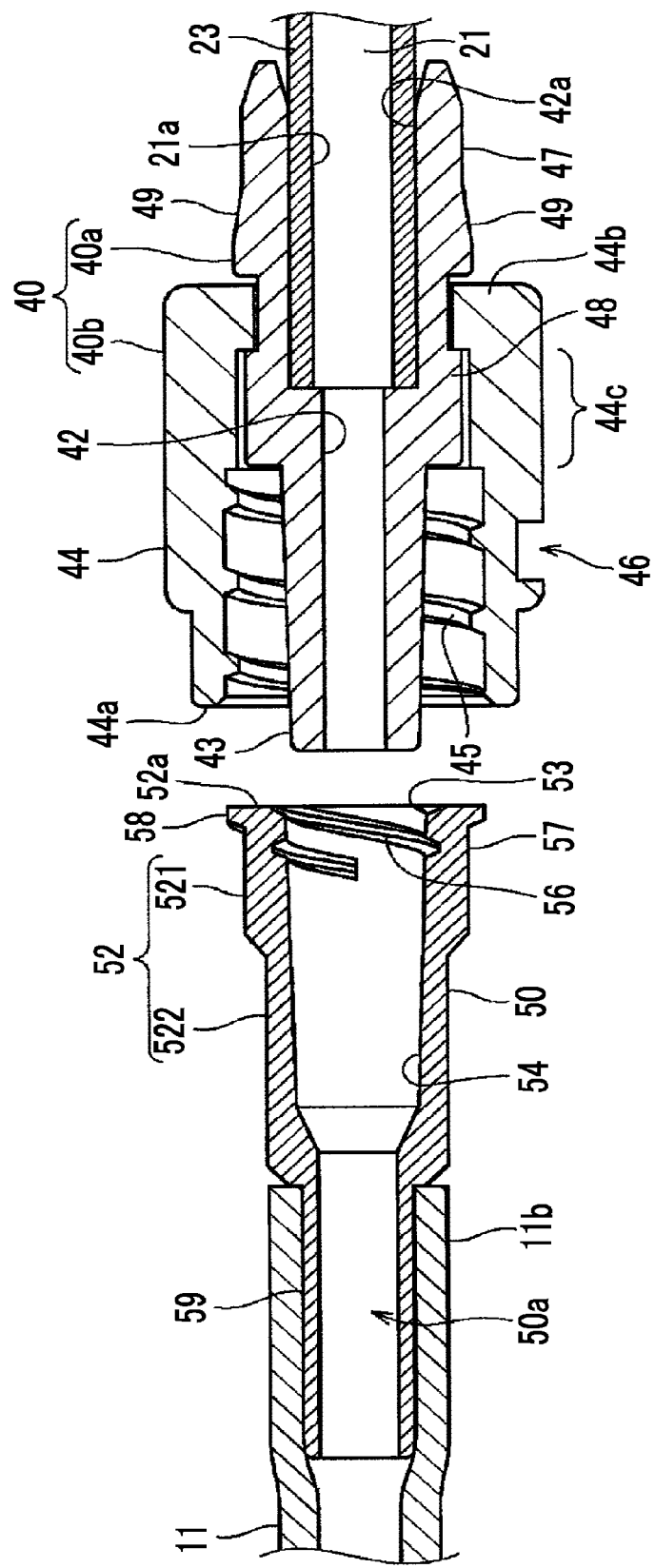
FIG. 17 is a cross-sectional view showing a modification example of the joint portion-side connector and shows a state where the female connector and the joint portion-side connector are separated from each other.

Moreover, for example, as in a modification example shown in FIG. 17, it is possible to use the joint portion-side connector 40 having a configuration in which the flexible tube 11 and the secondary tube 23 are axially rotatable with each other in a state where the female connector 50 and the joint portion-side connector 40 are connected to each other.

As shown in FIG. 17, the joint portion-side connector 40 according to this modification example is configured to include two members such as a first member 40a and a second member 40b.

The first member 40a is a hollow tube-shaped member, and a through-hole 42 is formed along an axis of the first member 40a.

The first member 40a has the male luer 43 on the tip side.

In the first member 40a, a portion adjacent to a base end side of the male luer 43 is a cylindrical large-diameter portion 48.

In addition, in the first member 40a, a portion (a base end portion of the first member 40a) adjacent to a base end side of the large-diameter portion 48 is a cylindrical small-diameter portion 47.

An outer diameter of the large-diameter portion 48 is larger than an outer diameter of the small-diameter portion 47 and is larger than an outer diameter of the male luer 43.

The through-hole 42 in a portion from the small-diameter portion 47 to the large-diameter portion 48 in the first member 40a is a secondary tube-fixing portion 42a having a diameter larger than those of the other portions in the through-hole 42.

On the outer surface of the small-diameter portion 47, a movement restricting rib 49 for restricting the second member 40b from relatively moving in the axial direction with respect to the first member 40a is formed.

Meanwhile, the second member 40b is a cylindrical member and is configured to include a tubular portion 44. Similarly to the structure described in Embodiment 1-1, the tubular portion 44 has a threaded portion 45 formed on an inner peripheral surface of the tubular portion 44.

In the second member 40b, a portion adjacent to a base end side of the tubular portion 44 is a cylindrical bearing portion 44c.

In the second member 40b, a portion (base end portion of the second member 40b) adjacent to the base end side of the bearing portion 44c is a cylindrical (ring-shaped) base end-side reduced diameter portion 44b.

An inner diameter of the bearing portion 44c is slightly larger than the outer diameter of the large-diameter portion 48 of the first member 40a.

An inner diameter of the base end-side reduced diameter portion 44b is smaller than the outer diameter of the large-diameter portion 48 of the first member 40a and is slightly larger than the outer diameter of the small-diameter portion 47 of the first member 40a.

Moreover, the small-diameter portion 47 is inserted into the base end-side reduced diameter portion 44b, and the large-diameter portion 48 is accommodated in the bearing portion 44c.

Therefore, the first member 40a and the second member 40b can mutually rotate around an axis.

Accordingly, in the state where the second member 40b of the joint portion-side connector 40 and the female connector 50 are connected to each other, the first member 40a, the second member 40b, and the female connector 50 can mutually rotate around the axis.

That is, in the state where the female connector 50 and the joint portion-side connector 40 are connected to each other, the flexible tube 11 and the secondary tube 23 are mutually rotatable around the axis.

Moreover, the first member 40a and the second member 40b are inhibited from mutually moving toward the axial direction. That is, if the second member 40b starts to move the left side in FIG. 17 relative to the first member 40a, the movement is restricted by the base end-side reduced diameter portion 44b interfering with the large-diameter portion 48. Conversely, if the second member 40b starts to move to the right side in FIG. 17 relative to the first member 40a, the movement is restricted by the base end-side reduced diameter portion 44b interfering with the movement restricting rib 49.

Moreover, the embodiments can be appropriately combined with each other within a scope which does not depart from the gist of the present invention.

The present embodiment include the following technical ideas.

(1) A coronary artery bypass surgery treatment tool including:
- a flexible tube;
- a suction cup in which an opening portion is formed to communicate with the flexible tube and which is provided at a distal end of the flexible tube;
- a joint portion which has a suction path;
- a male connector which is provided in one of a proximal end of the flexible tube and a distal end of the suction path of the joint portion; and
- a female connector which is provided in the other thereof and is detachably connected to the male connector.

(2) The coronary artery bypass surgery treatment tool according to (1), further including:
- a linear body whose one end side is fixed to the distal end of the flexible tube or the suction cup,
- wherein a linear body-side connector is provided on the other end side of the linear body, and wherein the linear body-side connector can be detachably connected to a flexible tube-side connector which is a connector provided at the proximal end of the flexible tube, out of the male connector and the female connector.

(3) The coronary artery bypass surgery treatment tool according to (2), wherein the linear body is led out from a peripheral surface around an axis of the linear body-side connector, wherein the linear body-side connector includes a connection portion which is disposed on one end side of the linear body-side connector and is connected to the flexible tube-side connector, and a tapered protrusion portion which is disposed on the other end side of the linear body-side connector.

(4) The coronary artery bypass surgery treatment tool according to (2), wherein the linear body-side connector includes a connection portion which is disposed on one end side of the linear body-side connector and is connected to the flexible tube-side connector, and wherein the linear body is led out from the other end side of the linear body-side connector.

(5) The coronary artery bypass surgery treatment tool according to (4), wherein a reinforcing portion which is reinforced more than the other portions of the linear body is formed in a portion near the linear body-side connector in the linear body.

(6) The coronary artery bypass surgery treatment tool according to any one of (2) to (5), wherein the flexible tube-side connector is the female connector, wherein the linear body-side connector is a second male connector which is connectable to the female connector, and wherein the linear body-side connector includes a main body portion and a connection portion which is a protrusion formed to protrude from the main body portion and inserted into the female connector.

(7) The coronary artery bypass surgery treatment tool according to (6), wherein the female connector includes a hollow accommodation portion which has an opening at one end and into which the connection portion is inserted from the opening, and wherein an engaging convex portion is formed in one of an outer peripheral surface of the connection portion and an inner peripheral surface of the accommodation portion, a helical engaging recessed portion is formed in the other thereof, and the engaging convex portion and the engaging recessed portion are screwed to each other so that the linear body-side connector and the female connector are detachably connected to each other.

(8) The coronary artery bypass surgery treatment tool according to (7), wherein the engaging convex portion is formed on the outer peripheral surface of the connection portion and the engaging recessed portion is formed on the inner peripheral surface of the accommodation portion.

(9) The coronary artery bypass surgery treatment tool according to (8), wherein the accommodation portion is a female luer in which an inner diameter of the accommodation portion decreases in a depth direction from the opening, wherein a second engaging convex portion is formed in the vicinity of the one end on an outer peripheral surface of the accommodation portion, wherein the male connector is provided at the distal end of the suction path of the joint portion, and wherein the male connector has a male luer lock structure which includes a male luer which is fitted to the female luer, a tubular portion which is provided around the male luer, and a threaded portion which is formed on an inner peripheral surface of the tubular portion and is screwed to the second engaging convex portion of the accommodation portion.

(10) A treatment tool part including:

a flexible tube;

a suction cup in which an opening portion is formed to communicate with the flexible tube and which is provided at one end of the flexible tube;

a linear body whose one end side is fixed to the one end of the flexible tube or the suction cup; and a female connector which has a hollow accommodation portion and is provided at the other end of the flexible tube, wherein the accommodation portion is a female luer which has an opening at one end and in which an inner diameter of the accommodation portion decreases in a depth direction from the opening, and a spiral groove is formed on an inner peripheral surface of the female luer.

(11) The treatment tool part according to (10), wherein a linear body-side connector connectable to the female connector is provided on the other end side of the linear body, wherein the linear body-side connector includes a main body portion and a connection portion which is a protrusion formed to protrude from the main body portion and inserted into the female connector, and wherein an engaging convex portion which is screwed to the spiral groove is formed on an outer peripheral surface of the connection portion.

Embodiment 2-1

First, Embodiment 2-1 will be described with reference to FIGS. 1 to 12(*b*).

As shown in FIGS. 7 and 8, a medical connector 200 according to the present embodiment includes the male connector (linear body-side connector 70) and the female connector 50 which is connected to the male connector.

The male connector (linear body-side connector 70) has the main body portion 71 and the insertion protrusion 72 which is formed to protrude from the main body portion 71.

The female connector 50 has the hollow accommodation portion 52 which accommodates the insertion protrusion 72.

The engaging convex portion 72*a* is formed in one of the outer peripheral surface of the insertion protrusion 72 and the inner peripheral surface 54 of the accommodation portion 52, and the engaging recessed portion 56 is formed in the other thereof.

Moreover, the engaging convex portion 72*a* and the engaging recessed portion 56 are screwed to each other, and thus, the male connector and the female connector 50.

According to the medical connector 200 of the present embodiment, the outer peripheral surface of the insertion protrusion 72 of the male connector (linear body-side connector 70) and the inner peripheral surface of the female connector 50 are screwed to each other. Accordingly, compared to a structure in which the inner peripheral surface of the tubular portion disposed around the insertion protrusion of the male connector and the outer peripheral surface of the female connector are screwed to each other, the male connector (linear body-side connector 70) can be made compact. Therefore, the entire medical connector 200 including the male connector (linear body-side connector 70) can be made compact.

Moreover, the medical device (for example, the coronary artery bypass surgery treatment tool 100 shown in FIG. 1 and the treatment tool part 10 shown in FIG. 3) according to the present embodiment includes the medical connector 200 according to the present embodiment.

In addition, respective components of the medical connector 200 according to the present embodiment do not need to exist separately independently. A plurality of components may be formed as one member, a component may be formed of a plurality of members, a component may be a portion of another component, and a portion of a component and a portion of another component may overlap each other.

In addition, respective components of the coronary artery bypass surgery treatment tool 100 according to the present embodiment do not need to exist separately independently. A plurality of components may be formed as one member, a component may be formed of a plurality of members, a component may be a portion of another component, and a portion of a component and a portion of another component may overlap each other.

Moreover, respective components of the treatment tool part 10 according to the present embodiment do not need to exist separately independently. A plurality of components may be formed as one member, a component may be formed of a plurality of members, a component may be a portion of another component, and a portion of a component and a portion of another component may overlap each other.

Hereinafter, the present embodiment will be described in more detail.

As shown in FIG. 1, for example, the coronary artery bypass surgery treatment tool 100 includes the plurality (for example, three) of treatment tool parts 10, the joint portion 20, and the suction source 30.

Among these, the treatment tool part 10 is configured to include the medical connector 200. Accordingly, the corollary artery bypass surgery treatment tool 100 is also configured to include the medical connector 200.

The suction tube 31 for suction is led out from the suction source 30. The distal end of the suction tube 31 is connected to the proximal end (the proximal end of the main tube 22 described below) of the joint portion 20.

As shown in FIG. 2, for example, the joint portion 20 includes the main tube 22, and a plurality of (for example, three) secondary tubes 23 divided into a plurality (for example, divided into three tube) of tubes from the distal end of the main tube 22.

The main tube 22 is a tubular member which allows gas to flow through the inside of the main tube 22 from the distal end to the proximal end of the main tube 22.

Moreover, each of the secondary tubes 23 is a tubular member which allows gas to flow through the inside of the secondary tube 23 from the distal end to the proximal end of the secondary tube 23.

The proximal end of each secondary tube 23 communicates with the distal end of the main tube 22. Therefore, a series of suction paths 21 are formed in the joint portion 20 from the proximal end of the main tube 22 to the distal ends of the respective secondary tubes 23.

Each secondary tube 23 has the three-way valve 24 for performing switching between the open state in which the gas can flow through the secondary tube 23 and the closed state in which the flow of the gas in the secondary tube 23 is blocked.

The joint portion-side connector 40 which is each male connector is provided at the distal end (that is, the distal end of the joint portion 20) of each secondary tube 23, and the joint portion-side connector 40 communicates with the suction path 21. That is, in the present embodiment, the joint portion-side connector 40 is provided at the distal end of the suction path 21 of the joint portion 20.

As shown in FIG. 5, the joint portion-side connector 40 includes the main body portion 41, the male luer 43 which protrudes from one end (the left end in FIG. 5) of the main body portion 41, and the tubular portion 44 which is disposed around the male luer 43 protruding from the one end of the main body portion 41.

The male luer 43 is formed in a tapered shape in which the male luer 43 is tapered toward the tip side (the left side in FIG. 5).

In addition, for example, the tip side of the male luer 43 protrudes further from the tip 44a of the tubular portion 44.

For example, the helical threaded portion 45 is formed on an inner peripheral surface of the tubular portion 44. That is, the tubular portion 44 has a female screw shape.

The through-hole 42 is formed in the joint portion-side connector 40 from the other end of the main body portion 41 to the tip of the male luer 43.

For example, a portion on the other end side of the main body portion 41 in the through-hole 42 is the secondary tube-fixing portion 42a having a diameter smaller than that of a portion on the tip side of the male luer 43 in the through-hole 42.

The distal end of the secondary tube 23 is fixed to the joint portion-side connector 40 by inserting the distal end of the secondary tube 23 into the secondary tube-fixing portion 42a.

As shown in FIG. 3, for example, the treatment tool part 10 includes the flexible tube 11, the suction cup 12 which is provided at the distal end 11a of the flexible tube 11, and the female connector 50 which is provided at the proximal end 11b of the flexible tube 11.

The treatment tool part 10 further includes the flexible linear body 60 and the linear body-side connector 70 which is a male connector.

For example, the connection member 13 is formed integrally with the suction cup 12.

The first insertion hole 13a and the second insertion hole 13b are formed in the connection member 13.

Although the shape of the connection member 13 is not particularly limited, for example, the connection member 13 is formed in a long shape on one side. Moreover, axial directions of the first insertion hole 13a and the second insertion hole 13b extend to be parallel in the longitudinal direction of the connection member 13.

Moreover, for example, opening directions of the first insertion hole 13a and the second insertion hole 13b are the same as each other.

The distal end 11a of the flexible tube 11 is inserted into the first insertion hole 13a, and thus, the distal end 11a is fixed. That is, the suction cup 12 is provided at the distal end 11a of the flexible tube 11 via the connection member 13.

The one end side 60a of the linear body 60 is inserted into the second insertion hole 13b, and thus, the one end side 60a is fixed. That is, in the case of the present embodiment, the one end side 60a of the linear body 60 is fixed to the distal end 11a of the flexible tube 11 via the connection member 13 and is fixed to the suction cup 12 via the connection member 13.

However, the present invention is not limited to this example. That is, the one end side 60a of the linear body 60 may be directly fixed to the suction cup 12, and the one end side 60a of the linear body 60 may be directly fixed to the distal end 11a of the flexible tube 11.

In this way, the one end side 60a of the linear body 60 is fixed to the distal end 11a of the flexible tube 11 or the suction cup 12.

Moreover, as described above, the opening directions of the first insertion hole 13a and the second insertion hole 13b are the same direction as each other. Accordingly, the flexible tube 11 and the linear body 60 are led out from the connection member 13 in the same direction as each other.

The suction cup 12 is formed in a bowl shape and has an opening portion 12a. In addition, it is preferable that an uneven shape be formed inside the suction cup 12 as necessary.

The opening portion 12a of the suction cup 12 communicates with the internal space of the flexible tube 11 through the internal space of the suction cup 12 and the internal space of the connection member 13.

In the state where the opening portion 12a of the suction cup 12 is applied to a heart of the living body, the gas in the internal space of the suction cup 12 is sucked by the suction source 30 via the internal space of the connection member 13, the internal space of the flexible tube 11, the internal space (through-hole 50a in FIG. 6) of the female connector 50, the internal space (through-hole 42 in FIG. 6) of the joint portion-side connector 40, the suction path 21 inside the joint portion 20, and the suction tube 31. Accordingly, the suction cup 12 adsorbs the heart. By holding the suction cup 12 at a desired position in this state, the heart can be maintained at the desired position.

Here, the linear body-side connector 70 will be described with reference to FIG. 7.

The linear body-side connector 70 is provided on the other end side 60b side of the linear body 60. The linear body-side connector 70 can be detachably connected to the female connector 50 (see FIG. 8).

As shown in FIG. 7, the linear body 60 is led out from the peripheral surface 70a around the axis of the linear body-side connector 70.

For example, the linear body-side connector 70 has the insertion protrusion 72 which is disposed on the one end side of the linear body-side connector 70 and is connected to the female connector 50, and the tapered protrusion portion 73 which is disposed on the other end side of the linear body-side connector 70.

The linear body-side connector 70 includes the main body portion 71, and the insertion protrusion 72 is a protrusion formed to protrude toward one side from the main body portion 71. The connection portion 72 is inserted into the female connector 50 as shown in FIG. 8.

Moreover, the protrusion direction of the protrusion portion 73 from the main body portion 71 and the protrusion direction of the insertion protrusion 72 from the main body portion 71 are opposite to each other.

For example, the linear body-side connector 70 is configured by assembling two members such as the first member 75 and the second member 76 to each other.

The first member 75 is configured to include the main body component 751 and the above-described protrusion portion 73.

The main body component 751 is a tubular portion constituting the main body portion 71.

The main body component 751 has one end side opened and the other end side (protrusion portion 73 side) closed.

In the main body component 751, the fixing hole 751a to which the other end side 60b of the linear body 60 is fixed, and the fitting hole 751b into which the second member 76 is fitted and fixed are formed.

The fixing hole 751a and the fitting hole 751b are disposed to be adjacent to each other and communicate with each other.

In the fixing hole 751a and the fitting hole 751b, the fitting hole 751b is disposed on an opening side of the main body component 751.

The cutout portion 751c is formed on an outer peripheral wall of a portion of the main body component 751 where the fitting hole 751b is formed.

The second member 76 includes the fitting portion 761 which is fitted into the fitting hole 751b of the first member 75 and the above-described insertion protrusion 72.

The recessed portion 761a is formed in the fitting portion 761.

The recessed portion 761a communicates with the fixing hole 751a and also communicates with the cutout portion 751c.

The linear body 60 having the other end side 60b fixed to the fixing hole 751a is led out (extracted) from the peripheral surface 70a of the linear body-side connector 70 via the inside of the recessed portion 761a and the cutout portion 751c.

The insertion protrusion 72 protrudes from the fitting portion 761 to one side.

The engaging convex portion 72a is formed on the outer peripheral surface of the insertion protrusion 72.

More specifically, the insertion protrusion 72 includes the columnar large-diameter portion 77 and the columnar small-diameter portion 78 having a diameter smaller than the large-diameter portion 77. The large-diameter portion 77 and the small-diameter portion 78 are disposed coaxially with each other and are connected to each other in the axial direction.

The fitting portion 761 is provided at an end portion of the large-diameter portion 77 opposite to the small-diameter portion 78 side.

The engaging convex portion 72a is formed on the outer peripheral surface of the large-diameter portion 77.

Here, as shown in FIG. 10, during a treatment using the coronary artery bypass surgery treatment tool 100, it is possible to grasp the protrusion portion 73 of the linear body-side connector 70 by forceps 91 and pull the treatment tool part 10.

Next, the female connector 50 will be described with reference to FIGS. 4(a), 4(b), and 4(c).

The female connector 50 is formed in a tubular shape as a whole. That is, the through-hole 50a (FIG. 4(c)) is formed from one end of the female connector 50 to the other end thereof.

A portion of the female connector 50 in the axial direction (axial direction of the through-hole 50a) of the female connector 50 constitutes an accommodation portion 52, and the remaining portion constitutes an insertion tubular portion 59.

The opening 53 is formed at the one end 52a of the accommodation portion 52. The insertion protrusion 72 of the linear body-side connector 70 is inserted into the accommodation portion 52 from the opening 53.

The helical engaging recessed portion 56 (spiral groove) is formed on the inner peripheral surface 54 of the accommodation portion 52.

In this way, the engaging convex portion 72a is formed on the outer peripheral surface of the insertion protrusion 72, and the engaging recessed portion 56 is formed on the inner peripheral surface of the accommodation portion 52.

The engaging recessed portion 56 of the accommodation portion 52 and the engaging convex portion 72a of the insertion protrusion 72 are screwed to each other, and thus, the female connector 50 and the linear body-side connector 70 are detachably connected to each other.

However, the present invention is not limited to this example. That is, the engaging convex portion 72a may be formed on the inner peripheral surface 54 of the accommodation portion 52 while the engaging recessed portion 56 may be formed on the outer peripheral surface of the insertion protrusion 72, the engaging recessed portion 56 and the engaging convex portion 72a are screwed to each other, and thus, the female connector 50 and the linear body-side connector 70 may be connected to each other.

In this way, the insertion protrusion 72 is inserted from the opening 53 formed at the one end 52a of the accommodation portion 52.

In addition, the accommodation portion 52 is a female luer in which the inner diameter of the accommodation portion 52 decreases in the depth direction from the opening 53. That is, the inner diameter of the accommodation portion 52 gradually decreases toward the left side in FIG. 5.

In addition, the second engaging convex portion 58 is formed in the vicinity of the one end 52a of the accommodation portion 52 on the outer peripheral surface of the accommodation portion 52.

Accordingly, the female connector 50 can be also connected to the joint portion-side connector 40.

Moreover, the one end 52a of the accommodation portion 52 is also one end of the female connector 50.

As can be seen from the above description, the female connector 50 (medical connector) according to the present embodiment can also be defined as follows.

That is, the female connector 50 is a medical connector which is a hollow female connector 50 which has the opening 53 on the one end 52a and whose inner diameter decreases in the depth direction from the opening 53, in which the protrusion portion (second engaging convex portion 58) is formed in the vicinity of the one end 52a on the outer peripheral surface of the female connector 50, and the helical recessed groove (engaging recessed portion 56) is formed on the inner peripheral surface of the female connector 50.

Accordingly, the female connector 50 can be connected to both the joint portion-side connector 40 and the linear body-side connector 70. Further, when the female connector 50 is connected to the joint portion-side connector 40, a luer-fitting structure can be realized.

Meanwhile, the male luer 43 (FIG. 5) of the joint portion-side connector 40 is formed in a shape which is fitted to the accommodation portion 52. The threaded portion 45 formed on the peripheral surface of the tubular portion 44 of the joint portion-side connector 40 is screwed to the second engaging convex portion 58 of the accommodation portion 52. That is, the joint portion-side connector 40 has the male her lock structure 46 which includes the male luer 43 which is fitted to the female luer (accommodation portion 52), the tubular portion 44 which is provided around the male luer 43, and the threaded portion 45 which is formed on the inner peripheral surface of the tubular portion 44 and is screwed to the second engaging convex portion 58 of the accommodation portion 52.

More specifically, the accommodation portion 52 of the female connector 50 includes the large-diameter portion 521 including the one end 52a and the small-diameter portion 522. An outer peripheral surface of the small-diameter portion 522 is formed to have a diameter smaller than the outer peripheral surface of the large-diameter portion 521.

The large-diameter portion 521 and the small-diameter portion 522 are disposed coaxially with each other and are connected to each other in an axial direction.

Moreover, the second engaging convex portion 58 is formed on the outer peripheral surface of the large-diameter portion 521. For example, the outer peripheral surface of the insertion tubular portion 59 is formed to have a diameter smaller than the outer peripheral surface of the small-diameter portion 522.

Moreover, for example, as shown in FIG. 10, the plurality of ribs 55 extending in the axial direction of the accommodation portion 52 may be formed on the outer peripheral surface of the small-diameter portion 522. In this case, since the ribs 55 prevent slipping, an operation of screwing the female connector 50 and the linear body-side connector 70 to each other can be performed more easily.

Figure 4:
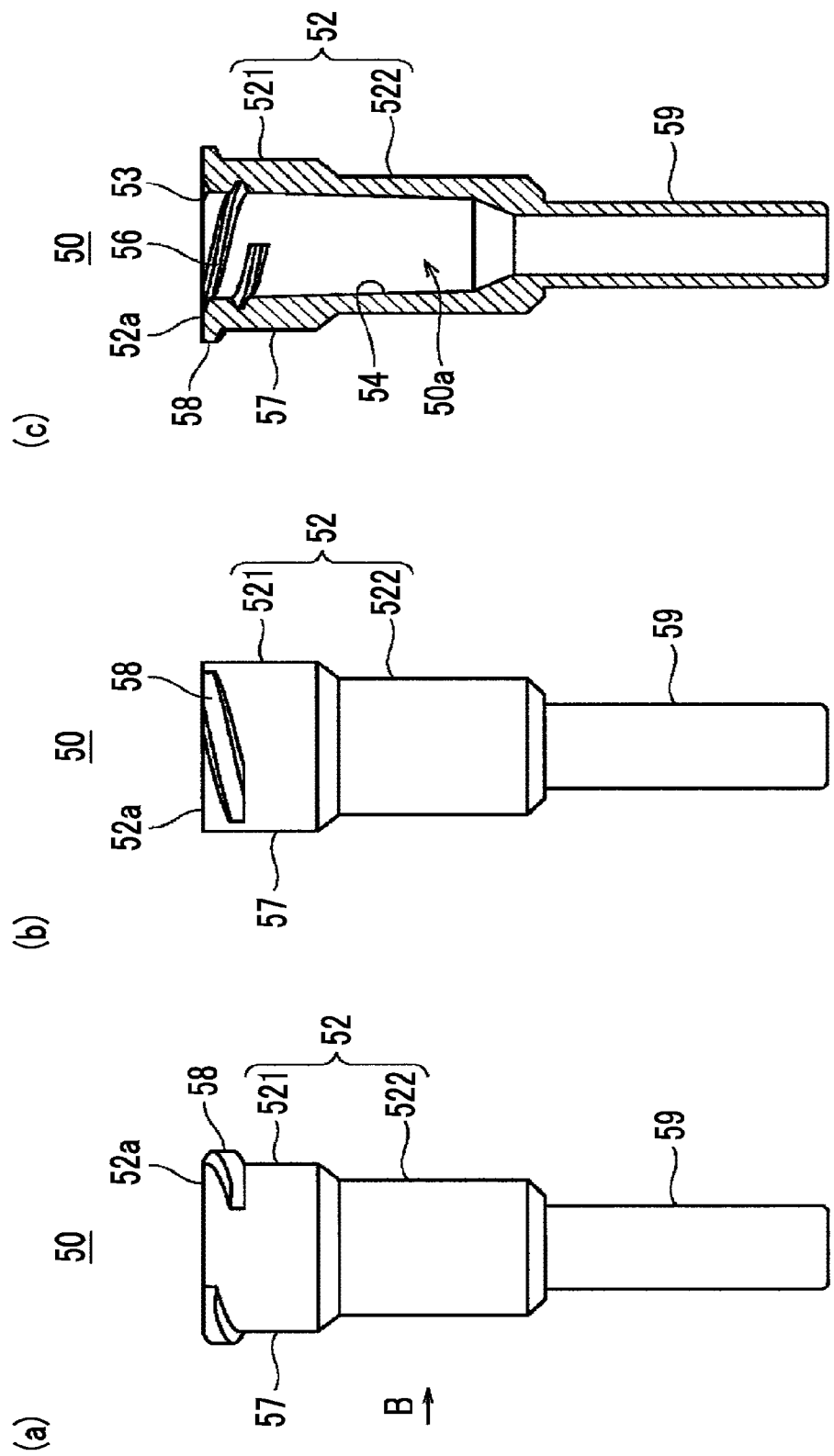
FIG. 4 is a view showing a flexible tube-side connector of the treatment tool part of the coronary artery bypass surgery treatment tool according to Embodiment 1-1, in which (a) is a side view, (b) is a side view when viewed in a direction of an arrow B in (a), and (c) is a cross-sectional view taken along a central axis of the flexible tube-side connector. In addition.

Moreover, the position at which the second engaging convex portion 58 is formed on the outer peripheral surface of the accommodation portion 52 of the female connector 50 may be separated from the one end 52a as in the examples shown in FIGS. 7, 8, and 10, or may be adjacent to one end 52a as in the examples shown in FIGS. 4(a), 4 (b), 4(c), 5, and 6. In any case, the female connector 50 is formed so as to be connectable to both the joint portion-side connector 40 and the linear body-side connector 70.

As shown in FIG. 5, the insertion tubular portion 59 is inserted into the proximal end 11b of the flexible tube 11, and thus, the female connector 50 is attached to the proximal end 11b of the flexible tube 11.

Here, the female connector 50 can be selectively detachably connected to one of the joint portion-side connector 40 and the linear body-side connector 70.

That is, as shown in FIG. 6, the male luer 43 is inserted into the accommodation portion 52 and the threaded portion 45 and the second engaging convex portion 58 are screwed to each other. Accordingly, the female connector 50 and the joint portion-side connector 40 can be connected to each other. In the state where the female connector 50 and the joint portion-side connector 40 are connected to each other, the male luer 43 and the accommodation portion 52 are fitted to each other and are in close contact with each other.

Further, as shown in FIG. 8, the insertion protrusion 72 is inserted into the accommodation portion 52 and the engaging convex portion 72a and the engaging recessed portion 56 are screwed to each other. Accordingly, the female connector 50 and the linear body-side connector 70 can be connected to each other. In addition, in the state where the female connector 50 and the linear body-side connector 70 are connected to each other, for example, the insertion protrusion 72 and the accommodation portion 52 are not in a fitted state and are not in close contact with each other.

Here, as shown in FIGS. 8 and 10, in the state (in order words, in the state where the linear body-side connector 70 and the female connector 50 are connected to each other) where the insertion protrusion 72 is inserted into the accommodation portion 52, the outer periphery of the second engaging convex portion 58 is flush with the outer peripheral surface of the main body portion 71 in the linear body-side connector 70 (male connector).

In other words, an outer diameter of the main body portion 71 of the linear body-side connector 70 and an outer diameter of the second engaging convex portion 58 of the female connector 50 are the same as each other, and in the state where the linear body-side connector 70 and the female connector 50 are connected to each other, the main body portion 71 and the second engaging convex portion 58 are coaxially disposed with each other.

Here, an example of a material of each component of the coronary artery bypass surgery treatment tool 100 will be described.

For example, the secondary tube 23, the flexible tube 11, and the linear body 60 are made of a soft resin, have flexibility, and can be bent flexibly.

For example, the suction cup 12 is made of a soft resin.

For example, each of the three-way valve 24, the joint portion-side connector 40, and the female connector 50 is made of a hard resin.

For example, the connection member 13 is made of a resin (hard resin or soft resin).

For example, the first member 75 of the linear body-side connector 70 is made of a resin (hard resin or soft resin).

For example, the second member 76 of the linear body-side connector 70 is made of a resin (hard resin or soft resin).

Next, an example of the treatment using the coronary artery bypass surgery treatment tool 100 will be described with reference to FIGS. 11, 12(*a*), and 12(*b*).

As shown in FIG. 11, the incision 93 which is the opening reaching the thoracic cavity 96 is formed on the chest wall 97 of the subject 92 such as a human body, and the heart 94 is exposed to the outside.

Meanwhile, the plurality of small incision holes 95 smaller than the incision 93 are formed in a portion around the incision 93 in the chest wall 97. The number of small incision holes 95 can be equal to the number of treatment tool parts 10 included in the coronary artery bypass surgery treatment tool 100, and in the present embodiment, for example, the number of the small incision holes is three.

Moreover, the indwelling sheath (not shown) may be provided in each small incision hole 95.

Next, in the treatment tool part 10 which is separated from the joint portion 20 and in which the female connector 50 and the linear body-side connector 70 are connected to each other, the female connector 50 and the linear body-side connector 70 of the treatment tool part 10 are disposed in the vicinity of the small incision hole 95 in the thoracic cavity 96.

Figure 12:
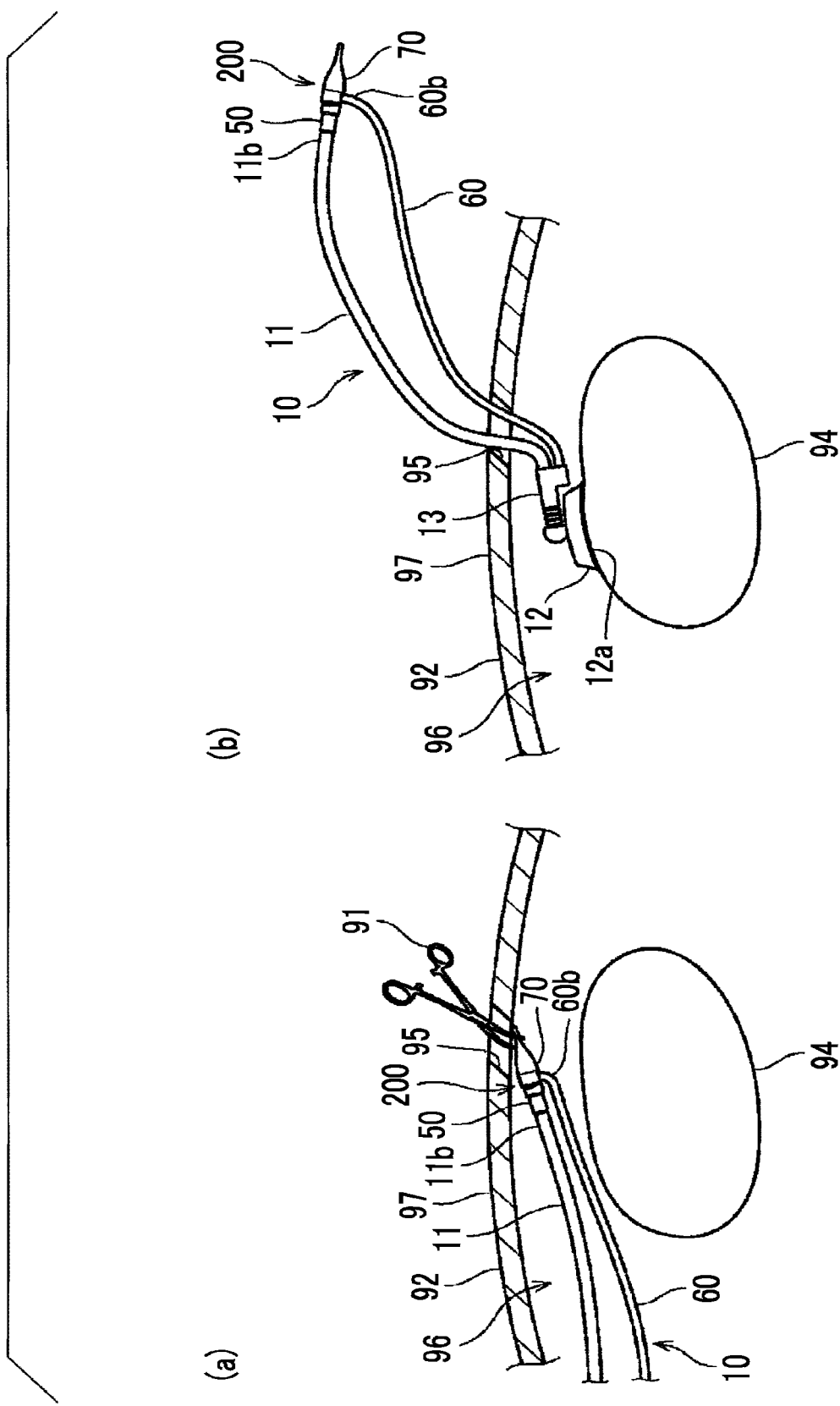
FIG. 12 is a schematic diagram explaining an example of the treatment using the coronary artery bypass surgery treatment tool according to Embodiment 1-1. Moreover.

Next, as shown in FIG. 12(*a*), the tip side of the forceps 91 is inserted into the thoracic cavity 96 via the small incision hole 95 from the outside of the subject 92, and the protrusion portion 73 of the linear body-side connector 70 of the treatment tool part 10 is grasped by the forceps 91.

Moreover, by pulling the forceps 91, the linear body-side connector 70 and the female connector 50, and a portion of the linear body 60 and a portion of the flexible tube 11 are extracted from the thoracic cavity 96 through the small incision hole 95. In addition, in this state, the suction cup 12 and the portion of the connection member 13 side in the treatment tool part 10 are located in the thoracic cavity 96.

Moreover, as shown in FIG. 12(*b*), the suction cup 12 is disposed in the vicinity of a desired adsorption site of the heart 94.

Further, the linear body-side connector 70 is separated from the female connector 50.

Moreover, the female connector 50 is connected to the male connector 40 of the joint portion 20 outside the subject 92.

This operation is repeated for each treatment tool part 10.

As a result, each treatment tool part 10 is connected to each joint portion-side connector 40 of the joint portion 20 (see FIG. 1).

Thereafter, the suction cup 12 of each treatment tool part 10 is applied to a desired adsorption site of the heart 94, the suction source 30 is activated, and each suction cup 12 is adsorbed to the heart 94.

In this way, the heart 94 can be held at a desired position.

Thereafter, the coronary artery bypass surgery can be performed.

Here, since each treatment tool part 10 can be separated from the joint portion 20, each treatment tool part 10 can be handled individually. Further, each treatment tool part 10 is inserted into the thoracic cavity 96 from the female connector 50 and the portion on the linear body-side connector 70 side, the linear body-side connector 70, the female connector 50, the linear body 60, and the flexible tube 11 are extracted from the thoracic cavity 96 via each small incision hole 95 using the forceps 91 or the like, and thereafter, the treatment tool part 10 can be connected to the joint portion 20.

Accordingly, the female connector 50, the linear body-side connector 70, a portion of the flexible tube 11, and a portion of the linear body 60 of each treatment tool part 10 can be extracted from each corresponding small incision hole 95.

Therefore, during the operation of disposing each suction cup 12 at a desired position and the subsequent coronary artery bypass surgery, the flexible tube 11 and the linear body 60 can be kept out of the way.

Accordingly, even if the incision 93 is made more compact than the related art, the coronary artery bypass surgery and a preparation thereof (disposition of the suction cup 12, or the like) can be suitably performed, thus, it is possible to reduce the burden on the living body.

According to the above-described first embodiment, the outer peripheral surface of the insertion protrusion 72 of the male connector (linear body-side connector 70) and the inner peripheral surface of the female connector 50 are screwed to each other. Accordingly, compared to a structure in which the inner peripheral surface of the tubular portion disposed around the insertion protrusion of the male connector and the outer peripheral surface of the female connector are screwed to each other, the male connector (linear body-side connector 70) can be made compact. Therefore, the entire medical connector 200 including the male connector (linear body-side connector 70) can be made compact.

Moreover, in the state where the insertion protrusion 72 is inserted into the accommodation portion 52, the outer periphery of the second engaging convex portion 58 is flush with the outer peripheral surface of the main body portion 71. Accordingly, as described with reference to FIGS. 12(*a*) and 12(*b*), it is possible to reduce a resistance when the medical connector 200 is extracted by the forceps 91 or the like via the small incision hole 95.

Moreover, for example, the outer diameter of the second engaging convex portion 58 has a minimum size necessary for the connection between the joint portion-side connector 40 and the second engaging convex portion 58. The fact that the outer diameter of the second engaging convex portion 58 is equal to the outer diameter of the main body portion 71 also means that the size of the main body portion 71 is as compact as possible.

Embodiment 2-2

Next, Embodiment 2-2 will be described with reference to FIGS. 13 to 18.

A medical connector 200 according to the present embodiment is different from the medical connector 200 according to Embodiment 2-1 as described below, and is configured similarly to the medical connector 200 according to Embodiment 2-1 in other respects.

That is, compared to the medical connector 200 according to Embodiment 2-1, in the medical connector 200 according to the present embodiment, a structure of a linear body-side connector 70 is different.

Moreover, a treatment tool part 10 (medical device: FIG. 13) according to the present embodiment is configured to include the medical connector 200 according to the present embodiment.

As shown in FIG. 14, in a case of the present embodiment, the linear body-side connector 70 includes the main body portion 71 and the insertion protrusion 72 which protrudes from one end of the main body portion 71.

Similarly to Embodiment 2-1, the insertion protrusion 72 is a portion which is connected to the female connector 50.

Similarly to Embodiment 2-1, the engaging convex portion 72a is formed on the outer peripheral surface of the insertion protrusion 72.

Figure 18:
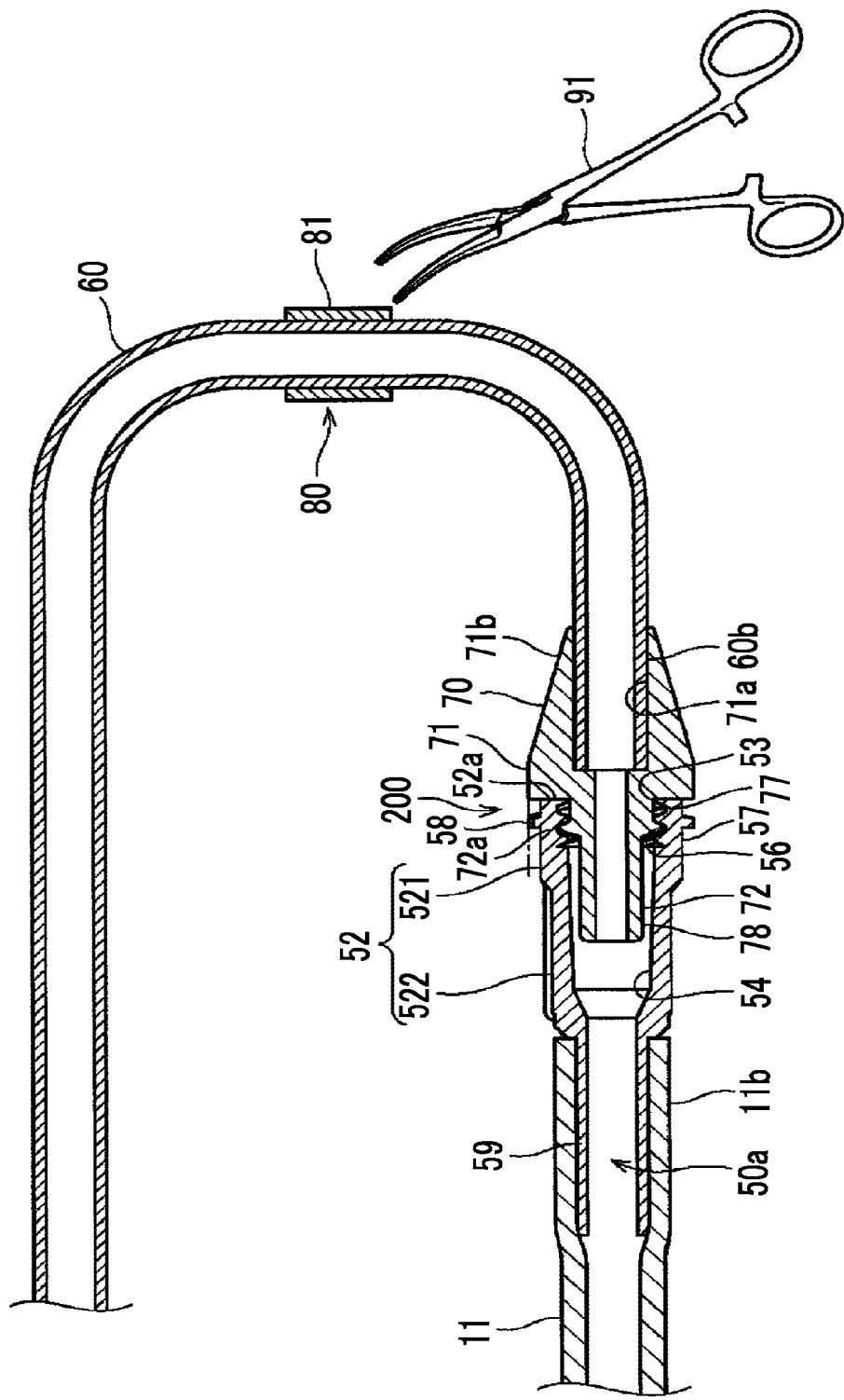
FIG. 18 is a cross-sectional view showing the female connector and the male connector of the medical connector according to Embodiment 2-2, and shows a state in which the female connector and the male connector are connected to each other.

In the case of the present embodiment, as shown in FIG. 18, the female connector 50 and the linear body-side connector 70 can be connected to each other.

Moreover, similarly to Embodiment 2-1, the insertion protrusion 72 has the large-diameter portion 77 and the small-diameter portion 78, and the engaging convex portion 72a is formed on the outer peripheral surface of the large-diameter portion 77.

The fixing hole 71a for fitting and fixing the other end side 60b of the linear body 60 is formed inside the main body portion 71.

Here, in the case of the present embodiment, a through-hole 79 is formed between both ends of the linear body-side connector 70.

That is, the linear body-side connector 70 (male connector) is a tubular body in which the through-hole 79 is formed between the main body portion 71 and the insertion protrusion 72.

In addition, the fixing hole 71a is configured by a portion of the through-hole 79.

However, the present invention is not limited to this example, and a portion (insertion protrusion 72 or the like) of the linear body-side connector 70 except for the fixing hole 71a may be a non-hollow structure, that is, a solid structure.

The outer peripheral surface of the main body portion 71 includes the tapered surface 71b which decreases in diameter toward the other end side (side opposite to the insertion protrusion 72 side) of the main body portion 71.

In the present embodiment, the linear body 60 is led out from a side opposite to the insertion protrusion 72 side in the main body portion 71.

In the case of the present embodiment, as shown in FIGS. 13 and 18, the reinforcing portion 80 which is reinforced more than the other portions of the linear body 60 is formed in a portion of the linear body 60 near the linear body-side connector 70.

For example, the reinforcing portion 80 is configured by a reinforcing tube 81 being externally fitted around the linear body 60.

In the case of the present embodiment, when the treatment tool part 10 is extracted from the thoracic cavity, the reinforcing portion 80 can be grasped by the forceps 91 as shown in FIG. 18. Accordingly, there is no need to directly grasp the linear body 60 or the flexible tube 11, and thus, damage to the linear body 60 or the flexible tube 11 can be suppressed.

In addition, for example, the plurality of grooves extending in an axial direction of the reinforcing tube 81 are formed on an outer peripheral surface of the reinforcing tube 81. Accordingly, it is possible to prevent the forceps 91 from slipping from the reinforcing tube 81 when the reinforcing tube 81 is grasped by the forceps 91.

In addition, a coronary artery bypass surgery treatment tool (the entire tool is not shown) according to the present embodiment is different from the coronary artery bypass surgery treatment tool 100 according to Embodiment 2-1 in that the treatment tool part 10 shown in FIG. 13 is provided instead of the treatment tool part 10 shown in FIG. 3, and the coronary artery bypass surgery treatment tool 100 according to the present embodiment is configured similarly to the coronary artery bypass surgery treatment tool 100 according to Embodiment 2-1 in other respects.

Moreover, since the outer peripheral surface of the main body portion 71 of the linear body-side connector 70 has the tapered surface 71b, it is possible to reduce a resistance when the treatment tool part 10 is extracted from the thoracic cavity.

Hereinbefore, the embodiments are described with reference to the drawings. However, the embodiments are examples of the present invention, and thus, various configurations other than the above-described embodiments can also be adopted.

For example, as in a modification example shown in FIG. 17, it is possible to use the joint portion-side connector 40 having a configuration in which the flexible tube 11 and the secondary tube 23 are axially rotatable with each other in a state where the female connector 50 and the joint portion-side connector 40 are connected to each other.

As shown in FIG. 17, the joint portion-side connector 40 according to this modification example is configured to include the two members such as the first member 40a and the second member 40b.

The first member 40a is a hollow tube-shaped member, and the through-hole 42 is formed along the axis of the first member 40a.

The first member 40a has the male luer 43 on the tip side.

In the first member 40a, the portion adjacent to the base end side of the male luer 43 is the cylindrical large-diameter portion 48.

In addition, in the first member 40a, the portion (the base end portion of the first member 40a) adjacent to the base end side of the large-diameter portion 48 is the cylindrical small-diameter portion 47.

The outer diameter of the large-diameter portion 48 is larger than the outer diameter of the small-diameter portion 47 and is larger than the outer diameter of the male luer 43.

The through-hole 42 in a portion from the small-diameter portion 47 to the large-diameter portion 48 in the first member 40a is the secondary tube-fixing portion 42a having a diameter larger than those of the other portions in the through-hole 42.

On the outer surface of the small-diameter portion 47, the movement restricting rib 49 for restricting the second member 40b from relatively moving in the axial direction with respect to the first member 40a is formed.

Meanwhile, the second member 40b is a cylindrical member and is configured to include the tubular portion 44. Similarly to the structure described in Embodiment 2-1, the tubular portion 44 has the threaded portion 45 formed on the inner peripheral surface of the tubular portion 44.

In the second member 40b, a portion adjacent to the base end side of the tubular portion 44 is the cylindrical bearing portion 44c.

In the second member 40b, a portion (base end portion of the second member 40b) adjacent to the base end side of the bearing portion 44c is the cylindrical (ring-shaped) base end-side reduced diameter portion 44b.

The inner diameter of the bearing portion 44c is slightly larger than the outer diameter of the large-diameter portion 48 of the first member 40a.

The inner diameter of the base end-side reduced diameter portion 44b is smaller than the outer diameter of the large-diameter portion 48 of the first member 40a and is slightly larger than the outer diameter of the small-diameter portion 47 of the first member 40a.

Moreover, the small-diameter portion 47 is inserted into the base end-side reduced diameter portion 44b, and the large-diameter portion 48 is accommodated in the bearing portion 44c.

Therefore, the first member 40a and the second member 40b can mutually rotate around an axis.

Accordingly, in the state where the second member 40b of the joint portion-side connector 40 and the female connector 50 are connected to each other, the first member 40a, the second member 40b, and the female connector 50 can mutually rotate around the axis.

That is, in the state where the female connector 50 and the joint portion-side connector 40 are connected to each other, the flexible tube 11 and the secondary tube 23 are mutually rotatable around the axis.

Moreover, the first member 40a and the second member 40b are inhibited from mutually moving toward the axial direction. That is, if the second member 40b starts to move to the left side in FIG. 17 relative to the first member 40a, the movement is restricted by the base end-side reduced diameter portion 44b interfering with the large-diameter portion 48. Conversely, if the second member 40b starts to move to the right side in FIG. 17 relative to the first member 40a, the movement is restricted by the base end-side reduced diameter portion 44b interfering with the movement restricting rib 49.

Moreover, the embodiments can be appropriately combined with each other within a scope which does not depart from the gist of the present invention.

The present embodiments include the following technical ideas.

(1) A medical connector, including:
a male connector; and
a female connector which is connected to the male connector,
wherein the male connector has a main body portion and an insertion protrusion which is formed to protrude from the main body portion,
wherein the female connector has a hollow accommodation portion which accommodates the insertion protrusion, and
wherein an engaging convex portion is formed in one of an outer peripheral surface of the insertion protrusion and an inner peripheral surface of the accommodation portion, an engaging recessed portion is formed in the other thereof, and the engaging convex portion and the engaging recessed portion are screwed to each other so that the male connector and the female connector are connected to each other.

(2) The medical connector according to (1),
wherein the engaging convex portion is formed on the outer peripheral surface of the insertion protrusion, and the engaging, recessed portion is formed on the inner peripheral surface of the accommodation portion.

(3) The medical connector according to (1) or (2),
wherein the insertion protrusion is inserted from an opening formed at one end of the accommodation portion, wherein the accommodation portion is a female luer in which an inner diameter of the accommodation portion decreases in a depth direction from the opening, and wherein a second engaging convex portion is formed in the vicinity of the one end of the accommodation portion on an outer peripheral surface of the accommodation portion.

(4) The medical connector according to (3),
wherein in a state where the insertion protrusion is inserted into the accommodation portion, an outer periphery of the second engaging convex portion is flush with an outer peripheral surface of the main body in the male connector.

(5) The medical connector according to any one of (1) to (4),
wherein the male connector is a tubular body in which a through-hole is formed between the main body portion and the insertion protrusion.

(6) A medical connector which is a hollow female connector having an opening at one end of which an inner diameter decreases in a depth direction from the opening,
wherein a protrusion portion is formed in the vicinity of the one end on an outer peripheral surface of the female connector, and
wherein a helical recessed groove is formed on an inner peripheral surface of the female connector.

(7) A medical device, including:
the medical connector according to any one of (1) to (6).

REFERENCE SIGNS LIST

10: treatment tool part (medical device)
11: flexible tube
11a: distal end
11b: proximal end
12: suction cup
12a: opening portion
13: connection member
13a: first insertion hole
13b: second insertion hole
20: joint portion
21: suction path
21a: distal end
22: main tube
23: secondary tube
24: three-way valve
30: suction source
31: suction tube
40: male connector, joint portion-side connector
40a: first member
40b: second member
41: main body portion
42: through-hole
42a: secondary tube-fixing portion
43: male luer
44: tubular portion
44a: tip
44b: base end-side reduced diameter portion
44c: bearing portion
45: threaded portion
46: male luer lock structure
47: small-diameter portion
48: large-diameter portion
49: movement restricting rib
50: female connector (flexible tube-side connector)
50a: through-hole
52: accommodation portion (female luer)

521: large-diameter portion
522: small-diameter portion
52a: one end
53: opening
54: inner peripheral surface
55: rib
56: engaging recessed portion (spiral groove)
58: second engaging convex portion
59: insertion tubular portion
60: linear body
60a: one end side
60b: the other end side
70: linear body-side connector (second male connector, male connector)
70a: peripheral surface
71: main body portion
71a: fixing hole
71b: tapered surface
72: connection portion (protrusion), insertion protrusion
72a: engaging convex portion
73: protrusion portion
75: first member
751: main body component
751a: fixing hole
751b: fitting hole
751c: cutout portion
76: second member
761: fitting portion
761a: recessed portion
77: large-diameter portion
78: small-diameter portion
79: through-hole
80: reinforcing portion
82: groove
91: forceps
92: subject
93: incision
94: heart
95: small incision hole
96: thoracic cavity
97: chest wall
100: coronary artery bypass surgery treatment tool (medical device)
200: medical connector

The invention claimed is:

1. A coronary artery bypass surgery treatment tool, comprising:
 a flexible tube;
 a joint portion having a suction path;
 a suction cup positioned at a distal end of the flexible tube and having an opening portion configured to communicate with the flexible tube;
 a male connector positioned in a distal end of the suction path of the joint portion;
 a female connector positioned in a proximal end of the flexible tube and detachably connected to the male connector;
 a linear body having one end side such that the one end side of the linear body is fixed to one of the suction cup and the distal end of the flexible tube; and
 a linear body-side connector having a connection portion on one end side thereof and a tapered protrusion portion on the other end side thereof such that the linear body-side connector is positioned on the other end side of the linear body and configured to be detachably connected to the female connector.

2. The coronary artery bypass surgery treatment tool according to claim 1, wherein the linear body-side connector includes a connection portion on one end side of the linear body-side connector and connected to the female connector.

3. A coronary artery bypass surgery treatment tool,
 a flexible tube;
 a joint portion having a suction path;
 a suction cup positioned at a distal end of the flexible tube and having an opening portion configured to communicate with the flexible tube;
 a male connector positioned in a distal end of the suction path of the joint portion;
 a female connector positioned in proximal end of the flexible tube and detachably connected to the male connector;
 a linear body having one end side such that the one end side of the linear body is fixed to one of the suction cup and the distal end of the flexible tube; and
 a linear body-side connector having a connection portion on one end side thereof and a tapered protrusion portion on the other end side thereof such that the linear body-side connector is positioned on the other end side of the linear body and configured to be detachably connected to the female connector,
 wherein the linear body has a reinforcing portion formed near the linear body-side connector and reinforced more than the other portions of the linear body.

4. The coronary artery bypass surgery treatment tool according to claim 1, wherein the linear body-side connector includes a main body portion and a connection portion which is a protrusion formed to protrude from the main body portion and inserted into the female connector.

5. The coronary artery bypass surgery treatment tool according to claim 4, wherein the female connector includes a hollow accommodation portion which has an opening at one end and into which the connection portion is inserted from the opening, and an engaging convex portion is formed in one of an outer peripheral surface of the connection portion and an inner peripheral surface of the accommodation portion, a helical engaging recessed portion is formed in the other one of the outer peripheral surface of the connection portion and the inner peripheral surface of the accommodation portion, and the engaging convex portion and the engaging recessed portion are screwed to each other such that the linear body-side connector and the female connector are detachably connected to each other.

6. The coronary artery bypass surgery treatment tool according to claim 5, wherein the engaging convex portion is formed on the outer peripheral surface of the connection portion, and the engaging recessed portion is formed on the inner peripheral surface of the accommodation portion.

7. The coronary artery bypass surgery treatment tool according to claim 6, wherein the accommodation portion is a female luer in which an inner diameter of the accommodation portion decreases in a depth direction from the opening, a second engaging convex portion is formed in the vicinity of the one end on an outer peripheral surface of the accommodation portion, the male connector is positioned at the distal end of the suction path of the joint portion, and the male connector has a male luer lock structure which includes a male luer which is fitted to the female luer, a tubular portion which is provided around the male luer, and a threaded portion which is formed on an inner peripheral surface of the tubular portion and is screwed to the second engaging convex portion of the accommodation portion.

8. A treatment tool part, comprising:
 a flexible tube;

a suction cup positioned at one end of the flexible tube and having an opening portion configured to communicate with the flexible tube;

a linear body having one end side fixed to the one end of the flexible tube or the suction cup;

a female connector having a hollow accommodation portion and positioned at the other end of the flexible tube; and a linear body-side connector having a connection portion on one end side thereof and a tapered protrusion portion on the other end side thereof such that the linear body-side connector is positioned on the other end side of the linear body and configured to be detachably connected to the female connector, wherein the accommodation portion is a female luer which has an opening at one end and in which an inner diameter of the accommodation portion decreases in a depth direction from the opening, and a spiral groove is formed on an inner peripheral surface of the female Luer.

9. The treatment tool part according to claim 8, wherein the linear body-side connector includes a main body portion, a connection portion which is a protrusion formed to protrude from the main body portion and inserted into the female connector, and an engaging convex portion which is screwed to the spiral groove is formed on an outer peripheral surface of the connection portion.

10. The coronary artery bypass surgery treatment tool according to claim 1, wherein the linear body having the one end side such that the linear body is fixed to the distal end of the flexible tube.

11. The coronary artery bypass surgery treatment tool according to claim 10, wherein the linear body-side connector includes a connection portion on one end side of the linear body-side connector and connected to the female connector.

12. The coronary artery bypass surgery treatment tool according to claim 10, wherein the linear body-side connector includes a main body portion and a connection portion which is a protrusion formed to protrude from the main body portion and inserted into the female connector.

13. The coronary artery bypass surgery treatment tool according to claim 12, wherein the female connector includes a hollow accommodation portion which has an opening at one end and into which the connection portion is inserted from the opening, and an engaging convex portion is formed in one of an outer peripheral surface of the connection portion and an inner peripheral surface of the accommodation portion, a helical engaging recessed portion is formed in the other one of the outer peripheral surface of the connection portion and the inner peripheral surface of the accommodation portion, and the engaging convex portion and the engaging recessed portion are screwed to each other such that the linear body-side connector and the female connector are detachably connected to each other.

14. The coronary artery bypass surgery treatment tool according to claim 13, wherein the engaging convex portion is formed on the outer peripheral surface of the connection portion, and the engaging recessed portion is formed on the inner peripheral surface of the accommodation portion.

15. The coronary artery bypass surgery treatment tool according to claim 14, wherein the accommodation portion is a female luer in which an inner diameter of the accommodation portion decreases in a depth direction from the opening, a second engaging convex portion is formed in the vicinity of the one end on an outer peripheral surface of the accommodation portion, the male connector is positioned at the distal end of the suction path of the joint portion, and the male connector has a male luer lock structure including a male luer configured to be fitted to the female luer, a tubular portion positioned around the male luer, and a threaded portion formed on an inner peripheral surface of the tubular portion and configured to be screwed to the second engaging convex portion of the accommodation portion.

16. The coronary artery bypass surgery treatment tool according to claim 1, wherein the female connector is a female luer, and the male connector has a male luer lock structure including a male luer configured to be fitted to the female luer.

17. The coronary artery bypass surgery treatment tool according to claim 14, wherein the accommodation portion is a female luer, and the male connector has a male luer lock structure including a male luer configured to be fitted to the female luer.

* * * * *